(12) United States Patent
Chaudhuri et al.

(10) Patent No.: US 12,140,595 B2
(45) Date of Patent: Nov. 12, 2024

(54) LIQUID BIOPSY TO DETECT CANCER EARLY AND SENSITIVELY IN PATIENTS WITH NEUROFIBROMATOSIS TYPE 1

(71) Applicants: Washington University, St. Louis, MO (US); NATIONAL INSTITUTES OF HEALTH, Bethesda, MD (US)

(72) Inventors: Aadel Chaudhuri, St. Louis, MO (US); Paul Jones, St. Louis, MO (US); Jeffrey Szymanski, St. Louis, MO (US); Angela Hirbe, St. Louis, MO (US); Russell Sundby, Baltimore, MD (US); John Shern, Bethesda, MD (US)

(73) Assignees: WASHINGTON UNIVERSITY, St. Louis, MO (US); NATIONAL INSTITUTES OF HEALTH, Bethesda, MD (US)

( * ) Notice: Subject to any disclaimer, the term of this patent is extended or adjusted under 35 U.S.C. 154(b) by 12 days.

(21) Appl. No.: 17/586,676

(22) Filed: Jan. 27, 2022

(65) Prior Publication Data

US 2022/0334121 A1    Oct. 20, 2022

Related U.S. Application Data

(60) Provisional application No. 63/142,207, filed on Jan. 27, 2021.

(51) Int. Cl.
*G01N 33/574* (2006.01)
*G16B 30/20* (2019.01)

(52) U.S. Cl.
CPC ....... *G01N 33/57488* (2013.01); *G16B 30/20* (2019.02)

(58) Field of Classification Search
CPC .................... G01N 33/57488; G16B 30/20
See application file for complete search history.

(56) References Cited

FOREIGN PATENT DOCUMENTS

WO    WO-2020094775 A1 *  5/2020  ......... C12N 15/1093

* cited by examiner

*Primary Examiner* — Mark Halvorson
*Assistant Examiner* — Dennis J Sullivan

(57) ABSTRACT

Among the various aspects of the present disclosure is the provision of methods for detecting cancer in Neurofibromatosis Type 1 (NF1) patients.

11 Claims, 31 Drawing Sheets

(30 of 31 Drawing Sheet(s) Filed in Color)

LIQUID BIOPSY TO DETECT CANCER EARLY AND SENSITIVELY IN PATIENTS WITH NEUROFIBROMATOSIS TYPE 1

CROSS-REFERENCE TO RELATED APPLICATIONS

This application claims the benefit of U.S. Provisional Application No. 63/142,207 filed Jan. 27, 2021 the contents of which are incorporated by reference in its entirety.

STATEMENT REGARDING FEDERALLY SPONSORED RESEARCH OR DEVELOPMENT

Not applicable.

MATERIAL INCORPORATED-BY-REFERENCE

Not applicable.

FIELD OF THE INVENTION

The present disclosure generally relates to methods and compositions for the detection of cancer in Neurofibromatosis Type 1 (NF1) patients.

BACKGROUND

Neurofibromatosis type 1 (NF1) is among the most common hereditary cancer predisposition syndromes worldwide. One-third of NF1 patients will develop a benign plexiform neurofibroma during their lifetime, and about half of these neurofibromas will transform into malignant peripheral nerve sheath tumors (MPNSTs). Early surgical resection of MPNSTs can be curative; however for more advanced cases chemotherapy and/or radiotherapy typically have low efficacy. Unfortunately, imaging is often unable to distinguish between MPNST and its benign precursor. Transformation from PN to MPNST is challenging to diagnose due to difficulties in distinguishing cross-sectional imaging results and intralesional heterogeneity resulting in biopsy sampling errors. Furthermore, complete excision of a plexiform neurofibroma may require a morbid procedure and thus should be avoided unless the tumor transforms. Therefore, there is a pressing need to detect MPNSTs early and distinguish them from their benign plexiform neurofibroma precursors.

Neurofibromatosis type 1 (NF1) is an autosomal dominant disorder affecting one in 3,000 individuals worldwide and is caused by a heterozygous inactivating mutation in the tumor suppressor gene, NF1, located on chromosome 17q11.2. NF1 encodes for the protein, neurofibromin 1, a negative regulator of the RAS signaling pathway. Thus, NF1 loss-of-function mutations lead to hyperactivated RAS, whose downstream effects contribute to the elevated cancer risk in NF1 patients. Approximately 50% of patients with NF1 develop histologically benign plexiform neurofibroma (PN), in which Schwann cells acquire biallelic inactivation of the NF1 gene. Histologically, PNs are heterogeneous, consisting of primarily S100-positive Schwann cells (60% to 80%), as well as fibroblasts, endothelial cells, perineural cells, smooth muscle cells, mast cells, interspersed axons, and pericytes. Imaging studies of PN mirror this heterogeneity, complicating the radiographic diagnosis of transformation to malignant peripheral nerve sheath tumor (MPNST), which occurs in 8% to 15% of patients with NF1, as well as the accuracy of diagnostic tissue biopsy.

MPNST are aggressive cancers with a poor prognosis that frequently arise from within their benign PN precursors. Due to rapid development of metastasis and resistance to both chemotherapy and radiotherapy, MPNST account for the majority of NF1-associated mortality with a 5-year survival rate of only 20%. Despite the high incidence and mortality of MPNST in the NF1 population, screening for malignant transformation and monitoring of MPNST is challenging. Clinical exam has poor sensitivity and may only signify MPNST when a PN lesion is showing sudden growth or causing severe pain. Serial PN biopsies are impractical as 9% to 21% of NF1 patients will have multiple PN, with varying levels of malignant potential requiring surveillance. Moreover, biopsies can yield false negative results due to geographic tumor heterogeneity resulting from MPNST arising from within heterogeneous PN precursor lesions. Furthermore, standard cross-sectional imaging cannot distinguish MPNST from PN with adequate specificity. Given the high prevalence of deadly MPNST in the context of a very common benign precursor lesion in a cancer-predisposed population, it is imperative that more reliable screening modalities be explored.

SUMMARY OF THE INVENTION

Among the various aspects of the present disclosure is the provision of methods and compositions for the detection of cancer (such as malignant peripheral nerve sheath tumor, MPNST) in patients with a diagnosis of Neurofibromatosis Type 1 (NF1). In various aspects, the methods are based on an analysis of reads obtained using whole genome sequencing (WGS) of cell-free DNA (cfDNA) obtained from plasma samples of a patient.

In one aspect, a method of predicting a transformation of a Neurofibromatosis Type 1 (NF1) condition into a malignant peripheral nerve sheath tumor (MPNST) condition in a patient is disclosed that includes providing a blood sample from the patient, isolating an amount of cell-free DNA (cfDNA) from the blood sample, performing ultra-low-pass whole genome sequencing (ULP-WGS) on the amount of cfDNA, comparing a read fragment size distribution of the plurality of reads to a reference read fragment size distribution, and predicting the transformation of the NF1 condition to the MPNST condition if the read fragment size distribution is enriched for shorter fragment sizes and depleted for longer fragment sizes. Performing a ULP-WGS includes fragmenting the amount of cfDNA to obtain a plurality of cfDNA fragments, constructing a DNA library that includes the plurality of cfDNA fragments, and sequencing the cfDNA fragments of the DNA library to obtain a plurality of reads, where each read includes a read sequence and a read fragment size corresponding to each cfDNA fragment. The reference read fragment size distribution corresponds to a population of non-MPNST patients. In some aspects, the read fragment size distribution and reference read fragment size distribution each include a distribution of fragment sizes ranging from about 90 bp to about 150 bp. In some aspects, the shorter fragment sizes include fragment sizes of less than about 138 bp and the larger fragment sizes include fragment sizes of at least about 138 bp. In some aspects, the method further includes aligning each read sequence of the plurality of reads to a reference human genome to obtain a plurality of aligned reads, estimating a plurality of local copy numbers based on the plurality of aligned reads, estimating a plurality of copy number alterations by comparing the plurality of local copy numbers to a plurality of reference copy numbers, estimating a tumor fraction of the patient based on the plurality of copy number alterations, predicting the transformation of the NF1 condition to the MPNST condition if the tumor fraction is larger than a threshold value, where the reference copy numbers include local copy numbers obtained from a population of non-MPNST patients. In some aspects, the threshold value ranges from about 0.01 to about 0.05. In some aspects, the threshold value is about 0.041. In some aspects, the ULP-WGS is performed at a genomic coverage ranging from about 0.3× to about 0.6×. In some aspects, the method further includes estimating a disease burden of the patient based on predetermined correlation between the estimated tumor fraction and the disease burden.

In another aspect, a method of predicting a transformation of a Neurofibromatosis Type 1 (NF1) condition into a transformation to a malignant peripheral nerve sheath tumor (MPNST) condition in a patient is disclosed that includes performing ultra-low-pass whole genome sequencing (ULP-WGS) on an amount of cfDNA isolated from a blood sample from the patient, aligning each read sequence of the plurality of reads to a reference human genome to obtain a plurality of aligned reads, estimating a plurality of local copy numbers based on the plurality of aligned reads, estimating a plurality of copy number alterations by comparing the plurality of local copy numbers to a plurality of reference copy numbers, wherein the reference copy numbers comprise local copy numbers obtained from a population of non-MPNST patients, estimating a tumor fraction of the patient based on the plurality of copy number alterations, and predicting the transformation of the NF1 condition to the MPNST condition if the tumor fraction is larger than a threshold value, Performing the ULP-WGS includes fragmenting the amount of cfDNA to obtain a plurality of cfDNA fragments, constructing a DNA library that includes the plurality of cfDNA fragments, and sequencing the cfDNA fragments of the DNA library to obtain a plurality of reads, in which each read includes a read sequence and a read fragment size corresponding to each cfDNA fragment. In some aspects, the read fragment size distribution and reference read fragment size distribution each include a distribution of fragment sizes ranging from about 90 bp to about 150 bp. In some aspects, the threshold value ranges from about 0.01 to about 0.05. In some aspects, the threshold value is about 0.041. In some aspects, the ULP-WGS is performed at a genomic coverage ranging from about 0.3× to about 0.6×.

In an additional aspect, a method of monitoring a malignant peripheral nerve sheath tumor (MPNST) condition in a patient is disclosed that includes providing a first blood sample and a second blood sample obtained from the patient at a first time and at a subsequent second time. The method further includes, for each of the first and second blood samples, performing ultra-low-pass whole genome sequencing (ULP-WGS) on an amount of cfDNA isolated from each blood sample, aligning each read sequence of the plurality of reads to a reference human genome to obtain a plurality of aligned reads, estimating a plurality of local copy numbers based on the plurality of aligned reads, estimating a plurality of copy number alterations by comparing the plurality of local copy numbers to a plurality of reference copy numbers, estimating a tumor fraction of the patient based on the plurality of copy number alterations, and comparing the first and second tumor fractions corresponding to the first and second blood samples, respectively, to determine the progression of the malignant peripheral nerve sheath tumor (MPNST) condition. Performing the ULP-WGS fragmenting the amount of cfDNA to obtain a plurality of cfDNA fragments, constructing a DNA library that includes the plurality of cfDNA fragments, and sequencing the cfDNA fragments of the DNA library to obtain a plurality of reads. The reference copy numbers compared to the plurality of local copy numbers from the patient sample include local copy numbers obtained from a population of non-MPNST patients. In some aspects, the read fragment size distribution and reference read fragment size distribution each include a distribution of fragment sizes ranging from about 90 bp to about 150 bp. In some aspects, the ULP-WGS is performed at a genomic coverage ranging from about 0.3× to about 0.6×. In some aspects, the method further includes monitoring an efficacy of a treatment to determine if is or is not responding to the treatment by comparing the first tumor fraction from the first blood sample obtained prior to or early in a treatment and the second tumor fraction from the second blood sample obtained during the treatment, wherein the patient is not responding to the treatment if the second tumor fraction is larger than the first tumor fraction, or the patient is responding to the treatment if the second tumor fraction is smaller than the first tumor fraction or if the second tumor fraction is unchanged from the first tumor fraction. In some aspects, the method further includes determining that the malignant peripheral nerve sheath tumor (MPNST) condition is in remission if the second tumor fraction is smaller than a threshold value. In other aspect, the threshold value ranges from about 0.01 to about 0.05. In other aspects, the threshold value is about 0.041.

Other objects and features will be in part apparent and in part pointed out hereinafter.

DESCRIPTION OF THE DRAWINGS

The patent or application file contains at least one drawing executed in color. Copies of this patent or patent application publication with color drawing(s) will be provided by the Office upon request and payment of the necessary fee.

Figure 1:
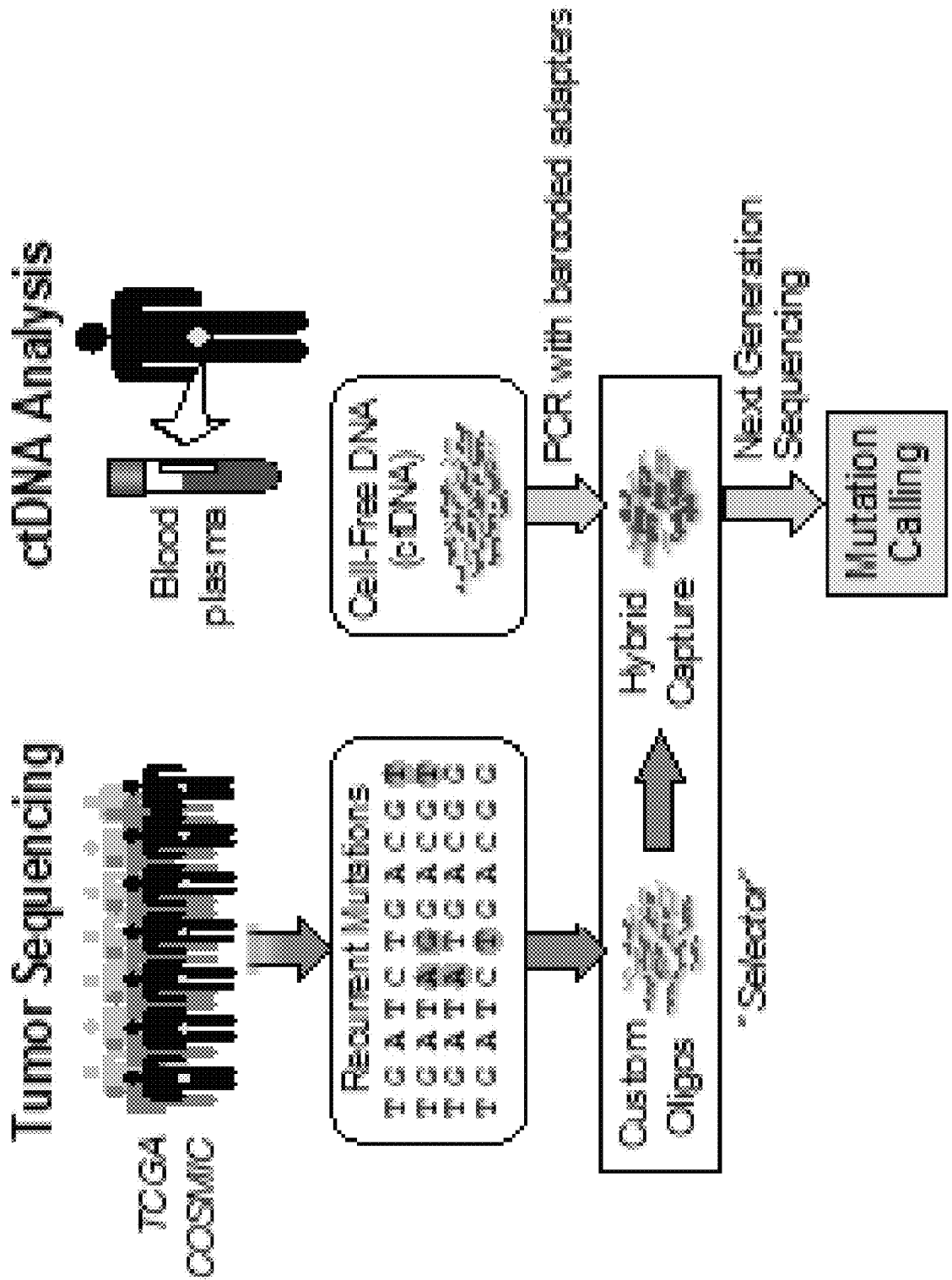
FIG. 1 is a flow chart illustrating a process used to design a hybrid capture panel, perform a targeted NGS using the hybrid capture panel, and perform ctDNA analysis of the targeted NGS data.

Those of skill in the art will understand that the drawings, described below, are for illustrative purposes only. The drawings are not intended to limit the scope of the present teachings in any way.

DETAILED DESCRIPTION OF THE INVENTION

The disclosed method enables early and sensitive identification of cancer in Neurofibromatosis Type 1 (NF1) patients, NF1 is among the most common hereditary disorders worldwide and is associated with a significantly increased risk of cancer. Many of these cancers occur during childhood or young adulthood, with potential to significantly reduce a patient's lifespan. Currently patients are followed by serial clinical and imaging exams, but several studies have shown that this approach lacks sensitivity for cancer screening and often leads to equivocal situations where it is unclear if an identified lesion is benign or malignant. Biopsy can be performed, however, it may lack sensitivity as well due to geographic heterogeneity (biopsy of benign vs. malignant region of a tumor). Biopsy can also be morbid, painful, and is not practical to perform for serial surveillance. To address this issue, we have developed a liquid biopsy approach to sensitively identify cancer in NF1 patients early. We expect it to be applicable to the millions of patients worldwide with a NF1 diagnosis who are at high risk for developing cancer. It will also be applicable to NF1 patients who already have cancer, as the disclosed assay also enables tumor burden tracking and treatment response vs. resistance assessment.

The disclosed method enables early and sensitive detection of cancer (such as malignant peripheral nerve sheath tumor) in patients with a diagnosis of Neurofibromatosis Type 1 (NF1) using a bio-fluids-based liquid biopsy approach. We do this through preparation of DNA isolated from blood plasma, followed by next-generation sequencing for genomic and epigenomic analysis (i.e. DNA methylation & hydroxymethylation), and a customized bioinformatic analysis approach. In this way we are able to predict which NF1 patients harbor malignancy earlier, and more sensitively than standard-of-care.

Specifically, we perform low-pass whole genome sequencing using a customized protocol that we developed for isolating, preparing and sequencing cell-free DNA from NF1 patients. We then perform analysis for copy number alterations, insertions/deletions, nucleotide variants, and genomic rearrangements. The disclosed assay relies primarily on genome-wide copy number analysis, and we demonstrate that patients harboring cancer have a distinct aberrant profile compared to those harboring benign disease after applying the disclosed custom protocol.

A specific technological advancement we implement is the ability to sensitively detect genome-wide copy number aberrations from cell-free DNA in Neurofibromatosis Type 1 patients, which is important for identifying cancer early.

The disclosed method identifies cancer in NF1 patients without requiring an invasive biopsy. This unique capability allows the disclosed noninvasive approach to be a clinically useful diagnostic tool which enables clinicians to identify cancer early, and select appropriate therapy for each patient in a personalized and precise fashion.

The disclosed method detects tumor genomic and epigenomic events in plasma. Traditional invasive tumor-based methods have shortcomings, including geographic tumor heterogeneity, such that important tumor clones can be missed in the biopsy specimen, leading to the incorrect conclusion upon analysis. The disclosed approach is based on analyzing tumor genomic and epigenomic events through biofluid (i.e. blood, urine) analysis, where geographic tumor heterogeneity should not be an issue. The disclosed novel approach can be used to flexibly detect tumor genomic and epigenomic alterations from nearly any bio-fluid or tissue type.

The disclosed method enables simultaneous assessment of genomic and epigenomic alterations including copy number alterations, genomic rearrangements, nucleotide variations and insertions/deletions. In this way we can query the oncogenomic status of a patient's tumor through the disclosed liquid biopsy approach.

The disclosed method can be used to identify cancer early, as well as track response to treatment and identify recurrence early. We do this by applying the disclosed assay at serial timepoints to monitor genomic/epigenomic changes that occur over time.

The disclosed method enables simultaneous tracking of genomic events relevant to the patient's solid tumor malignancy (mutations, fusions, copy number alterations) as well as clonal hematopoiesis (mutations in the genes DMT3A, TET2 and ASXL1). In this way we can delineate genomic events related to the patient's primary malignancy vs. potentially confounding clonal hematopoiesis mutations.

Figure 10:
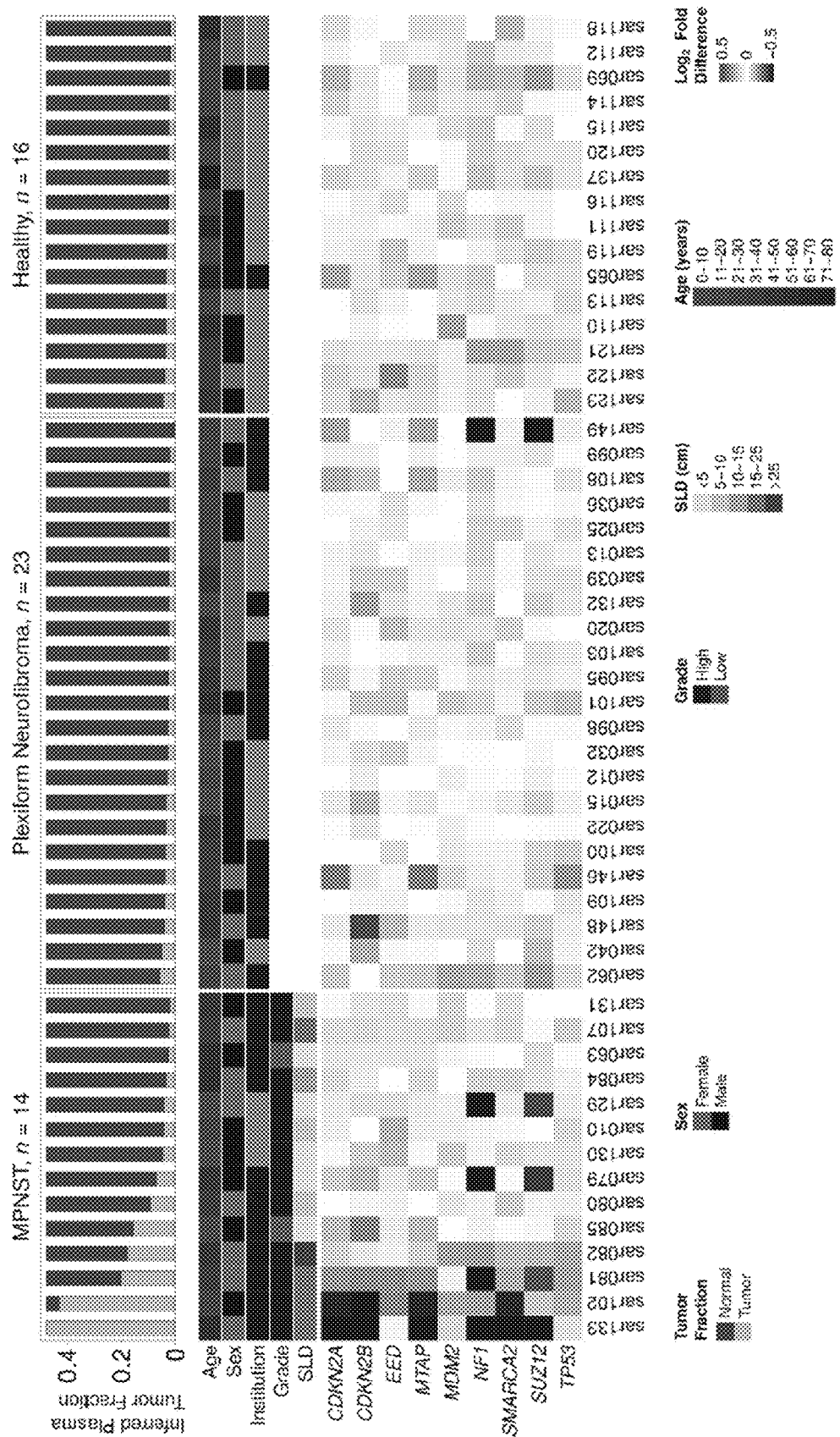
FIG. 10 is a heatmap summarizing individual subject demographics, copy number alterations (CNAs), and tumor fractions estimated from CNAs from a subject population that included normal controls, PN1 patients, and MPNST patients.
Figure 11A:
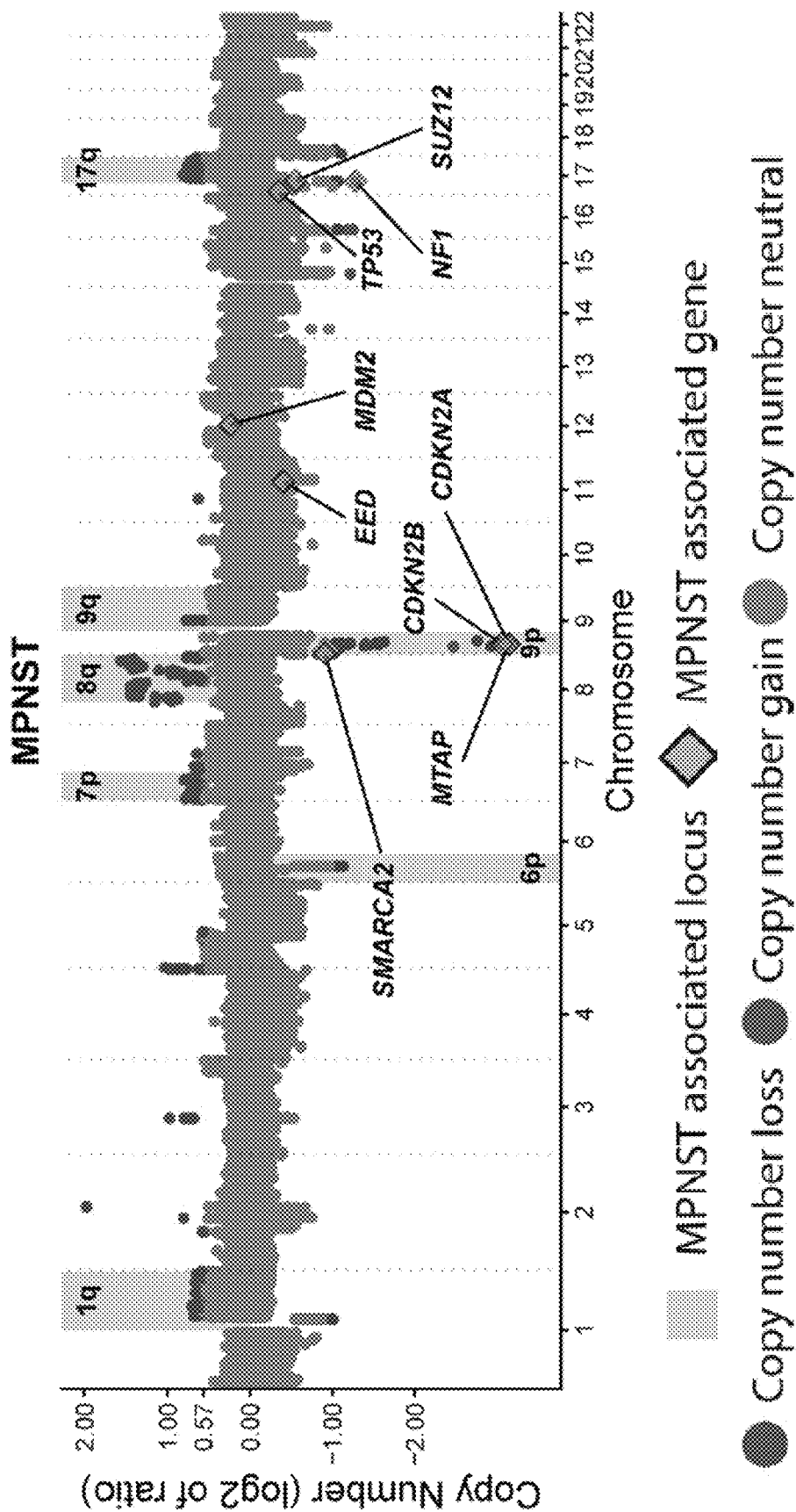
FIG. 11A is a graph summarizing copy number alterations obtain using ULP-WGS of plasma samples from a population of MPNST patients (n=46).
Figure 11B:
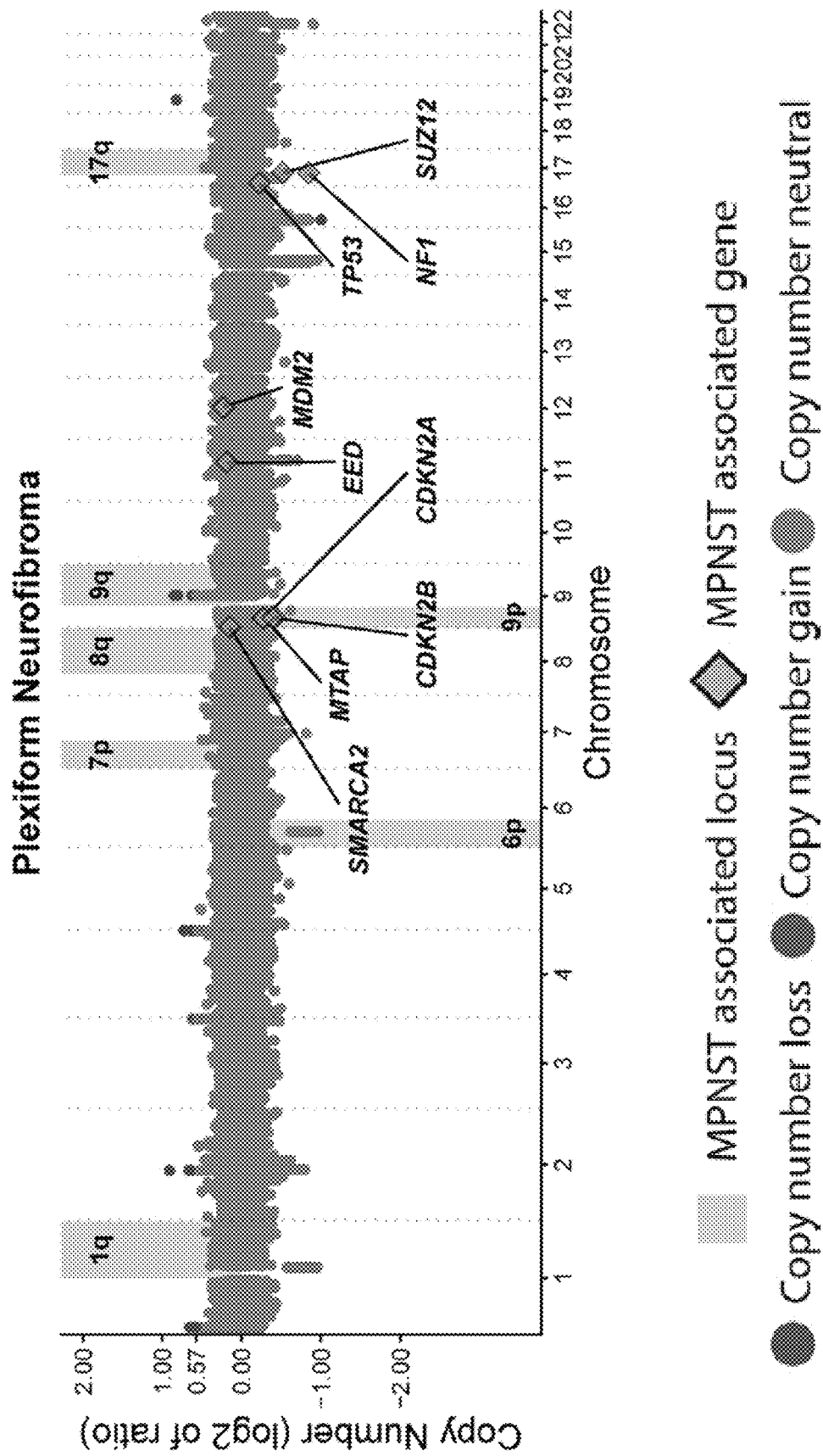
FIG. 11B is a graph summarizing copy number alterations obtain using ULP-WGS of plasma samples from a population of PN patients (n=23).
Figure 11C:
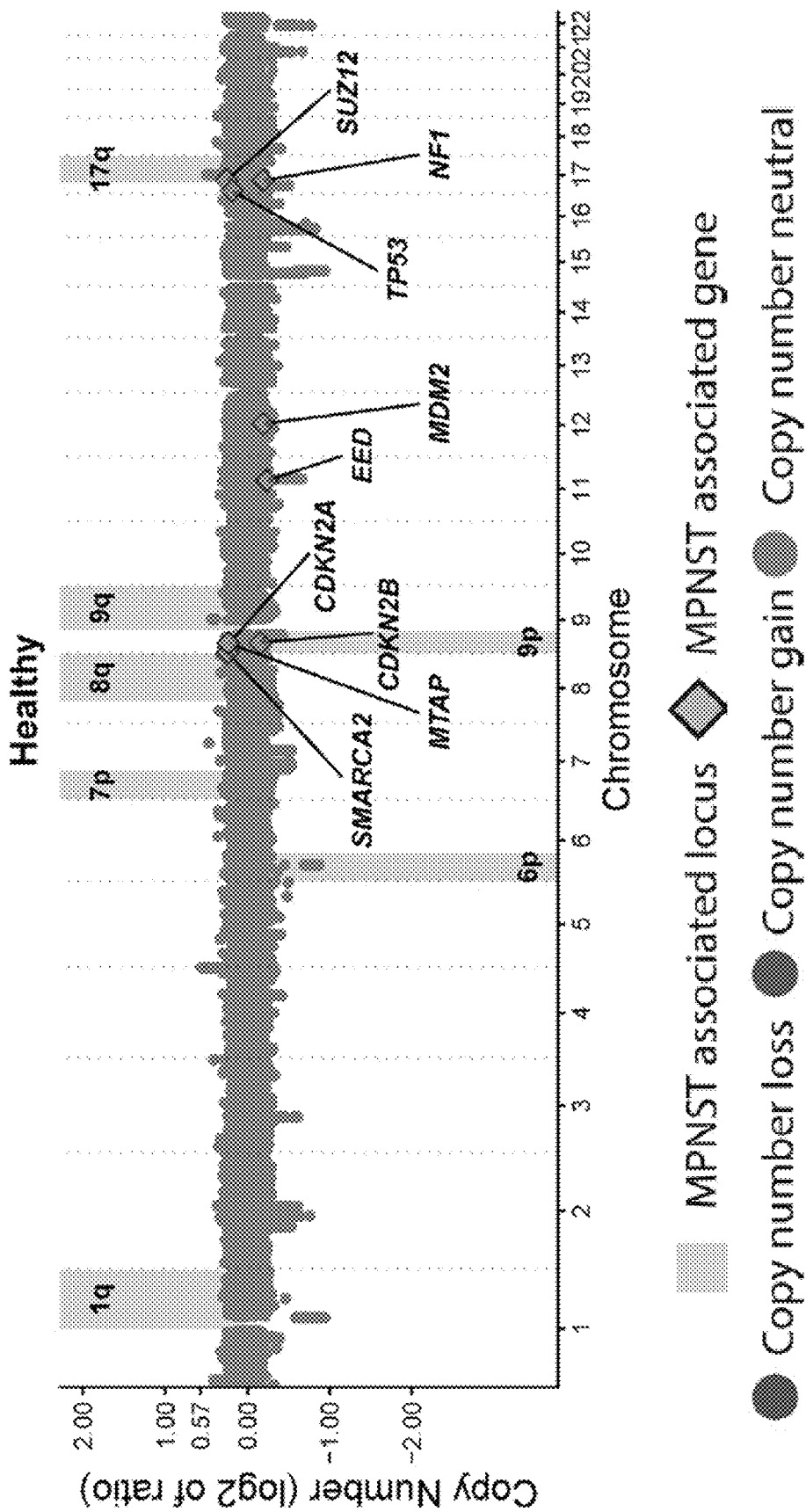
FIG. 11C is a graph summarizing copy number alterations obtain using ULP-WGS of plasma samples from a healthy control group (n=16).

As demonstrated in the Examples below, patients with MPNST were observed to harbor a unique cfDNA fragmentation profile and have significantly greater tumor genomic instability evident in plasma compared to PN patients. Further. cfDNA analysis was used to dynamically track treatment response in MPNST patients, potentially with greater precision than standard cross-sectional imaging. Copy number-altered genomic loci characteristic of malignant transformation from PN were accurately identified using ULP-WGS of cfDNA (FIGS. 10 and 11A). Specifically, loss of CDKN2A/B, SMARCA2, and SUZ12 were commonly found only in MPNST plasma samples, while loss of NF1 was observed in both MPNST and PN plasma (FIGS. 11A and 11B), but not healthy controls (FIG. 11C).

Figure 17:
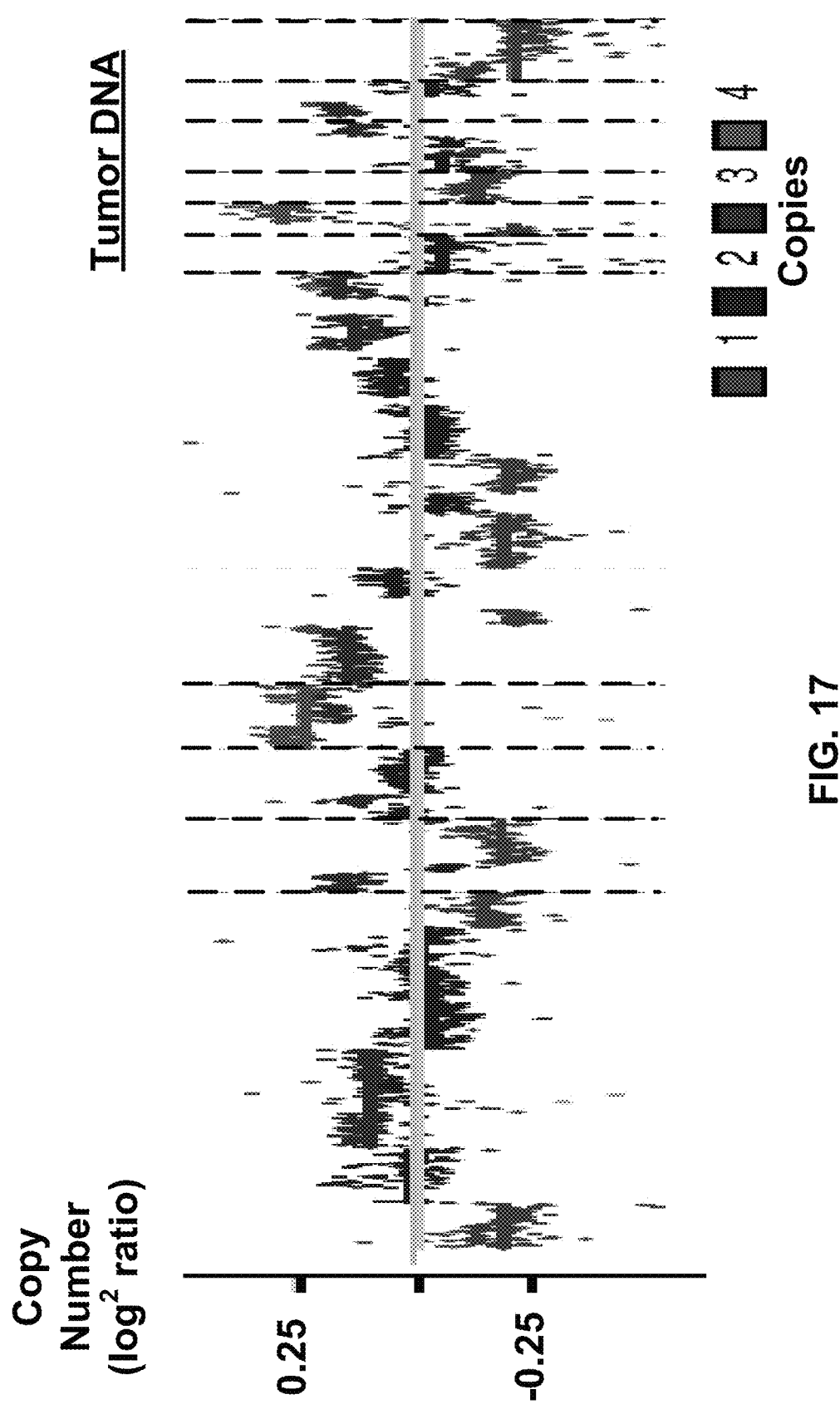
FIG. 17 contains a series of graphs comparing genome-wide CNAs assessed in 4 specimen types from a single MPNST patient (sar081): tumor tissue DNA, pretreatment blood plasma cfDNA, posttreatment cfDNA, and germline DNA from pretreatment PBMCs. Log 2 of copy number ratio is shown across the genome. Color scale depicts estimated copy number within the tumor fraction as determined by ichorCNA.
Figure 17:
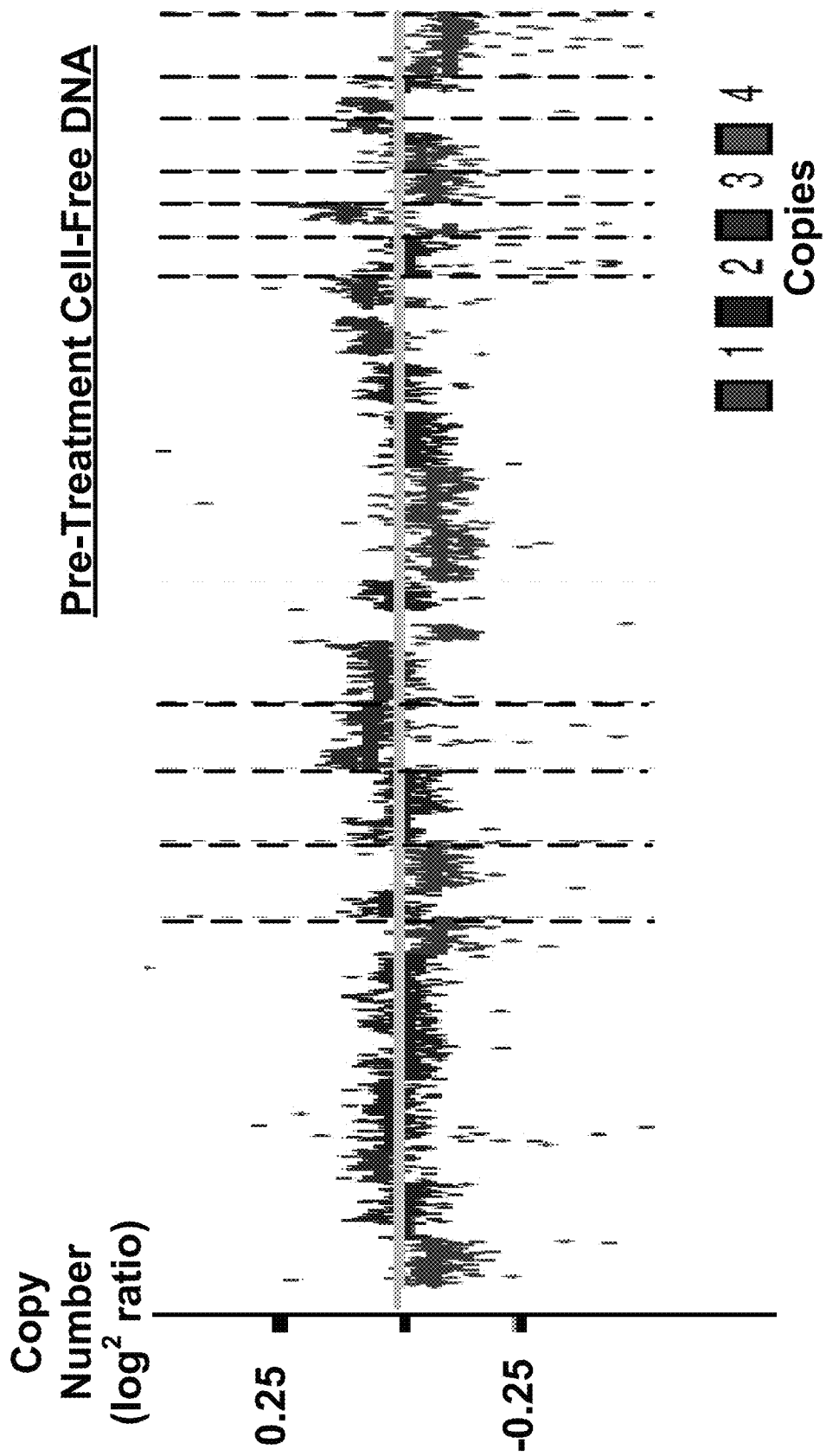
Figure 17:
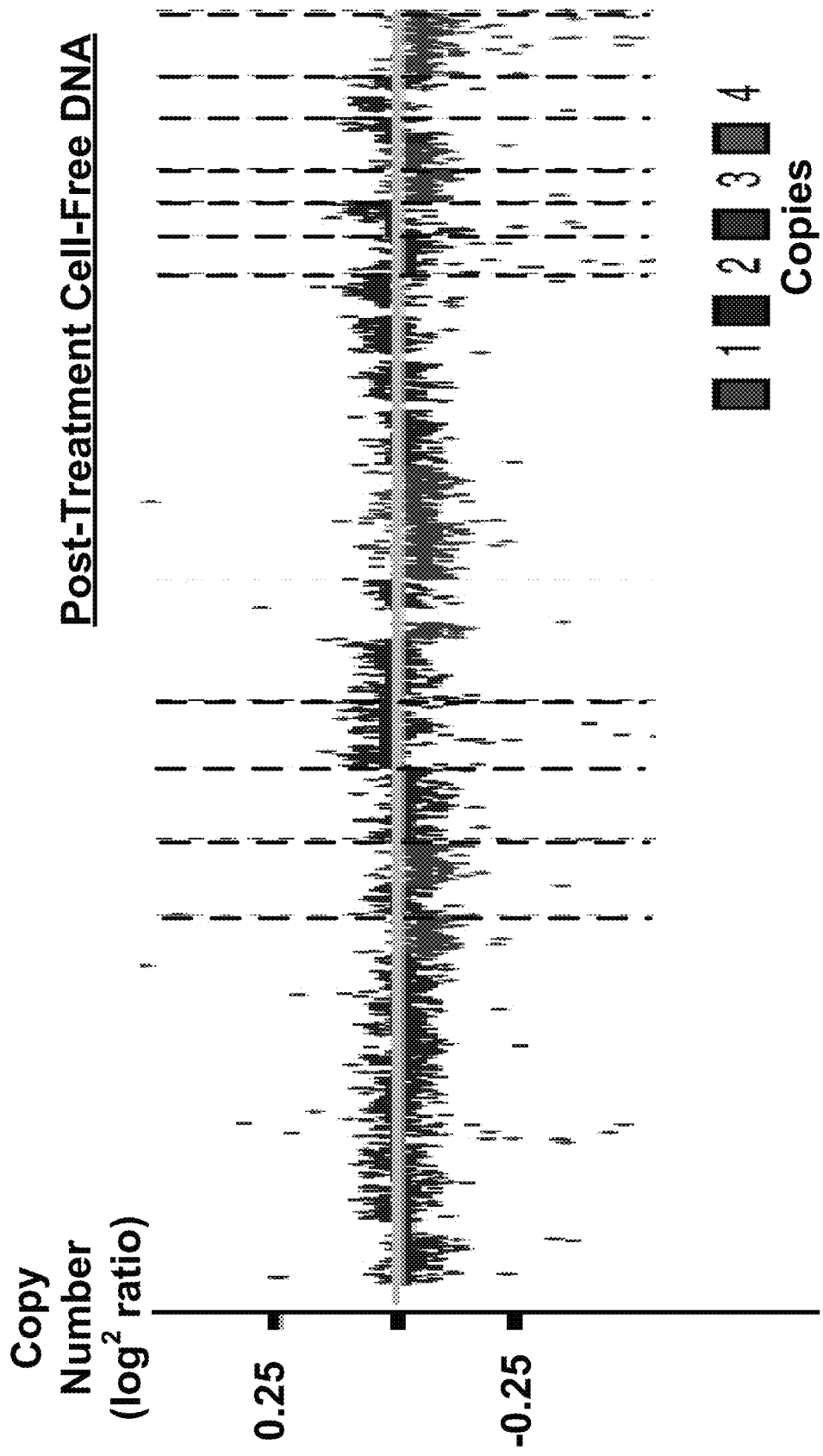
Figure 17:
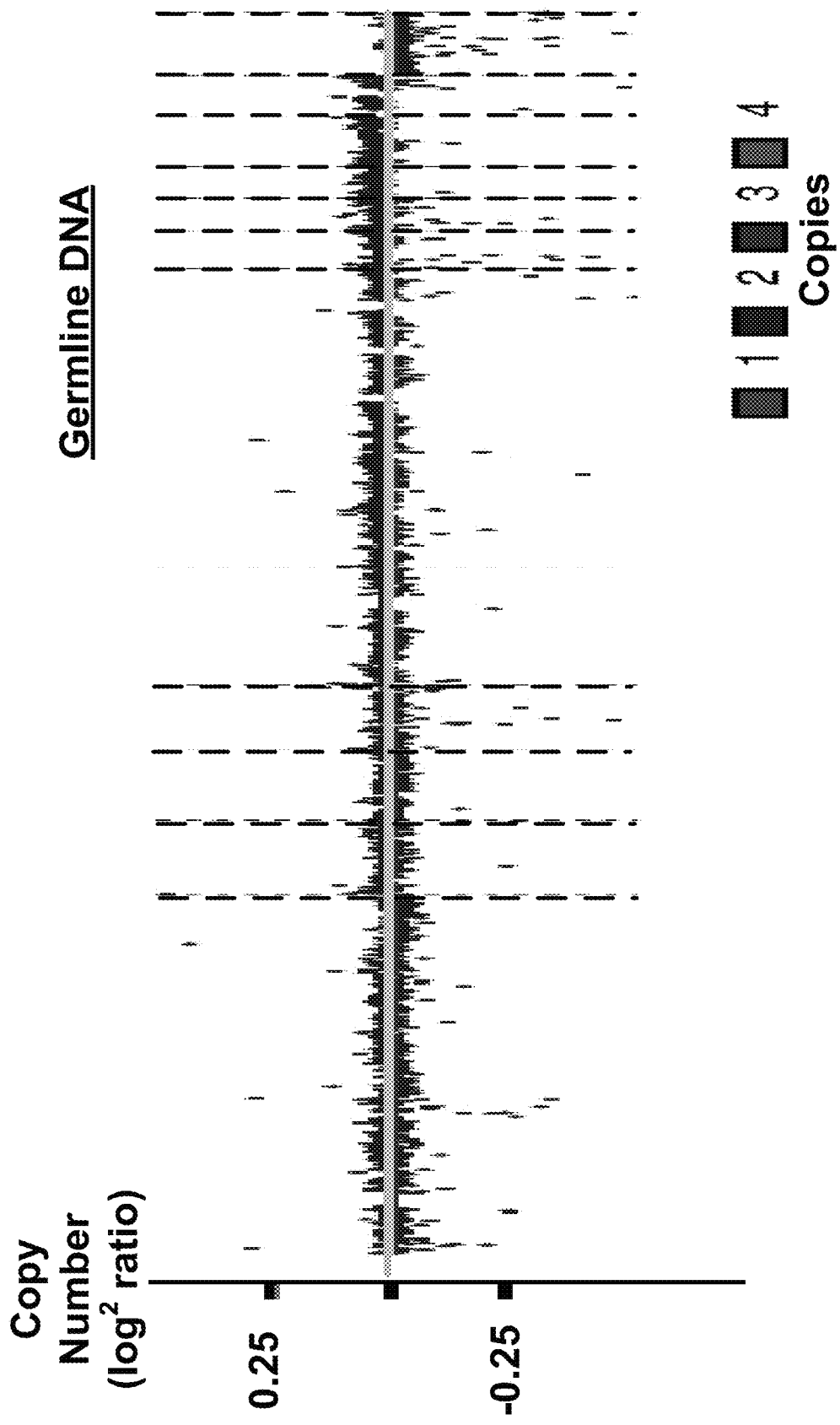

When paired tumor was available, plasma cfDNA-detected CNAs recapitulated tissue patterns of genomic instability (FIG. 17). Taken together, the data disclosed in the Examples demonstrate that even at low sequencing coverage, the genomic features of both NF1 and of progression from PN to MPNST are detectable in affected patients' plasma.

Figure 12B:
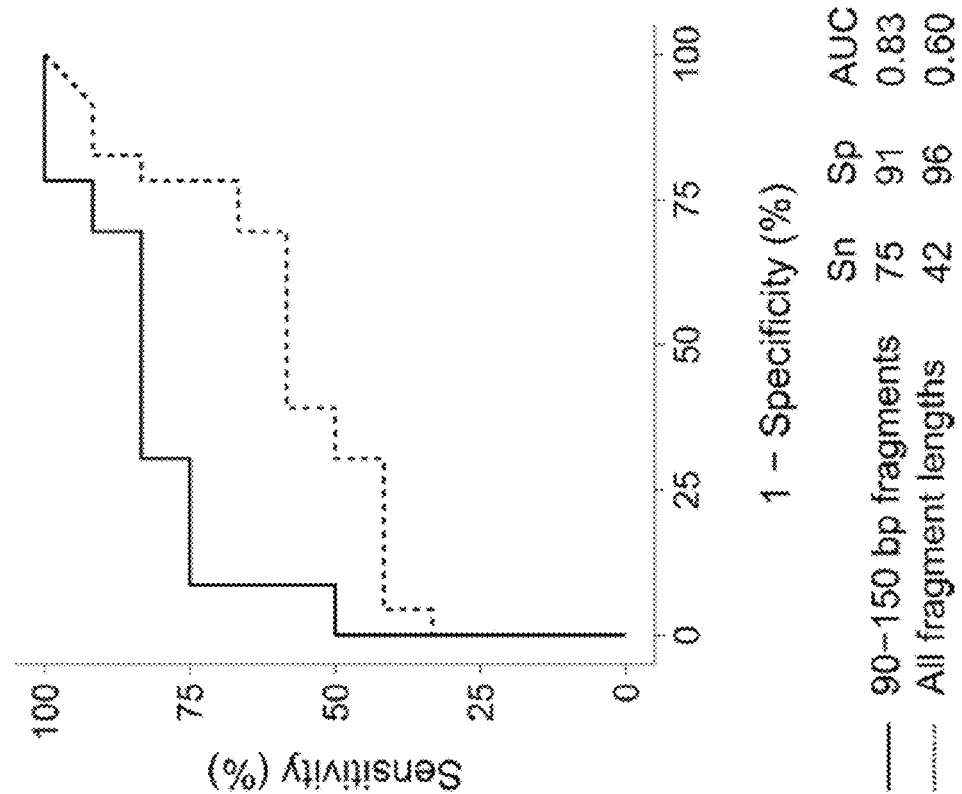
FIG. 12B is an ROC of plasma cfDNA tumor fraction comparing pretreatment MPNST to PN patients; solid line represents tumor fraction data derived only from 90-150 bp fragments and dotted line represents tumor fractions derived from all fragment lengths.

The Examples described below further demonstrate that cfDNA tumor fraction derived from genome-wide CNAs after selecting for shorter fragment lengths, without applying prior knowledge of patient-specific mutational profiles, differentiated MPNST from PN with high specificity (91%) and moderate sensitivity (75%) pretreatment (FIG. 12B) and both high specificity (91%) and sensitivity (83%) when measured serially (Table 3). The Examples demonstrate the use of cfDNA-based tumor fraction as a valuable adjunct to aid in monitoring patients with PN with the goal of early cancer detection.

Currently, malignant transformation in NF1 patients is difficult to screen for due to overlapping clinical symptoms and radiographic findings that are also associated with benign PN. Current standard practice for PN surveillance is to obtain imaging only when clinically indicated. Moreover, clinical surveillance for symptoms such as lesion-associated pain have a low specificity for identifying MPNST on subsequent workup. As described above, the results disclosed in the Examples demonstrate the use of cfDNA-based tumor fraction as a valuable adjunct to aid in monitoring patients with PN with the goal of early cancer detection.

In various aspects, the disclosed method of predicting a transformation of a Neurofibromatosis Type 1 (NF1) condition into a malignant peripheral nerve sheath tumor (MPNST) condition in a patient is performed non-invasively by subjecting a patient sample containing cell-free DNA to whole genome sequencing. In some aspects, the patient sample may be a blood sample that is centrifuged and further treated to isolate the cfDNA sample using any suitable known method without limitation, including the methods described in the Examples herein.

In various aspect, the cfDNA sample is subjected to whole genome sequencing using any suitable known method including, but not limited to, next-generation sequencing and other fast-throughput whole genome sequencing methods. In some aspects, the whole genome sequencing method used is ultra-low-pass whole genome sequencing (ULP-WGS).

In various aspects, the whole genome sequencing may include targeted sequencing using any known method without limitation including, but not limited to, a targeted sequencing method developed as described in the Examples below. Without being limited to any particular theory, the targeted sequencing enhances the sensitivity of the results by selectively sequencing those portions of the genome associated with the transformation from a PN1 condition to a MPNST condition.

In other aspects, the method may include producing a read fragment size distribution from the results of the whole genome sequencing. As described in th Examples below, it was discovered that the read fragment size distribution of the cfDNA samples from MPNST differed significantly from the corresponding read fragment size distributions from normal heathy controls or NF1 patients. In various aspects, the MPNST read fragment size distributions were found to be enriched for shorter fragment sizes and depleted for longer fragment sizes.

In some aspects, to enhance the sensitivity of this differential read fragment size distribution, read fragment size distributions are limited to fragment sizes ranging from about 90 bp to about 150 bp. In various other aspects, subsequent analysis of copy number alterations are performed based on read sequences limited to fragment sizes ranging from about 90 bp to about 150 bp.

In various aspects, the reads resulting from WGS are further analyzed to assess copy number variations relative to copy numbers associated with a reference condition including, but not limited to, a healthy normal condition or a NF1 condition. Specific copy number variations include, but are not limited to, any of the copy number variations described in the Examples below.

In various additional aspects, the copy number variations may be used to estimate a tumor fraction using any known method without limitation including, but not limited to, the use of software such as ichorCNA. In various aspects, the estimated tumor fraction is compared to a threshold value to determine whether the patient is at risk for development of MPNST or the extent of MPNST in the patient. In some aspects, serial blood samples may be obtained and analyzed, and the resulting estimated tumor fractions may be compared to determine if the tumor fraction increased or decreased over time, indicated progression or remission of MPNST, respectively. In other aspects, serial blood samples may be obtained and analyzed during various time points over a course of treatment to assess the efficacy of a treatment, and treatments may be terminated, altered, or continued based on changes in successive estimated of tumor fractions. In other additional aspects, serial blood samples may be obtained and analyzed to monitor for reoccurrence of an MPNST in a patient that is currently in remission.

The scope of the method is not limited to blood plasma-derived cell-free DNA. It can be applied to DNA derived from any bodily fluid including, but not limited to, urine and saliva.

Molecular Engineering

The following definitions and methods are provided to better define the present invention and to guide those of ordinary skill in the art in the practice of the present invention. Unless otherwise noted, terms are to be understood according to conventional usage by those of ordinary skill in the relevant art.

The terms "heterologous DNA sequence", "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

Expression vector, expression construct, plasmid, or recombinant DNA construct is generally understood to refer to a nucleic acid that has been generated via human intervention, including by recombinant means or direct chemical synthesis, with a series of specified nucleic acid elements that permit transcription or translation of a particular nucleic acid in, for example, a host cell. The expression vector can be part of a plasmid, virus, or nucleic acid fragment. Typically, the expression vector can include a nucleic acid to be transcribed operably linked to a promoter.

A "promoter" is generally understood as a nucleic acid control sequence that directs transcription of a nucleic acid. An inducible promoter is generally understood as a promoter that mediates transcription of an operably linked gene in response to a particular stimulus. A promoter can include necessary nucleic acid sequences near the start site of transcription, such as, in the case of a polymerase II type promoter, a TATA element. A promoter can optionally include distal enhancer or repressor elements, which can be located as much as several thousand base pairs from the start site of transcription.

A "transcribable nucleic acid molecule" as used herein refers to any nucleic acid molecule capable of being transcribed into a RNA molecule. Methods are known for introducing constructs into a cell in such a manner that the transcribable nucleic acid molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present disclosure, conventional compositions and methods for preparing and using constructs and host cells are well known to one skilled in the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754).

The "transcription start site" or "initiation site" is the position surrounding the first nucleotide that is part of the transcribed sequence, which is also defined as position +1. With respect to this site all other sequences of the gene and its controlling regions can be numbered. Downstream sequences (i.e., further protein encoding sequences in the 3' direction) can be denominated positive, while upstream sequences (mostly of the controlling regions in the 5' direction) are denominated negative.

"Operably-linked" or "functionally linked" refers preferably to the association of nucleic acid sequences on a single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. The two nucleic acid molecules may be part of a single contiguous nucleic acid molecule and may be adjacent. For example, a promoter is operably linked to a gene of interest if the promoter regulates or mediates transcription of the gene of interest in a cell.

A "construct" is generally understood as any recombinant nucleic acid molecule such as a plasmid, cosmid, virus, autonomously replicating nucleic acid molecule, phage, or linear or circular single-stranded or double-stranded DNA or RNA nucleic acid molecule, derived from any source, capable of genomic integration or autonomous replication, comprising a nucleic acid molecule where one or more nucleic acid molecule has been operably linked.

A constructs of the present disclosure can contain a promoter operably linked to a transcribable nucleic acid molecule operably linked to a 3' transcription termination nucleic acid molecule. In addition, constructs can include but are not limited to additional regulatory nucleic acid molecules from, e.g., the 3'-untranslated region (3' UTR). Constructs can include but are not limited to the 5' untranslated regions (5' UTR) of an mRNA nucleic acid molecule which can play an important role in translation initiation and can also be a genetic component in an expression construct. These additional upstream and downstream regulatory nucleic acid molecules may be derived from a source that is native or heterologous with respect to the other elements present on the promoter construct.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism such as a bacterium, cyanobacterium, animal or a plant into which a heterologous nucleic acid molecule has been introduced. The nucleic acid molecule can be stably integrated into the genome as generally known in the art and disclosed (Sambrook 1989; Innis 1995; Gelfand 1995; Innis & Gelfand 1999). Known methods of PCR include, but are not limited to, methods using paired primers, nested primers, single specific primers, degenerate primers, gene-specific primers, vector-specific primers, partially mismatched primers, and the like. The term "untransformed" refers to normal cells that have not been through the transformation process.

"Wild-type" refers to a virus or organism found in nature without any known mutation.

Design, generation, and testing of the variant nucleotides, and their encoded polypeptides, having the above required percent identities and retaining a required activity of the expressed protein is within the skill of the art. For example, directed evolution and rapid isolation of mutants can be according to methods described in references including, but not limited to, Link et al. (2007) Nature Reviews 5(9), 680-688; Sanger et al. (1991) Gene 97(1), 119-123; Ghadessy et al. (2001) Proc Natl Acad Sci USA 98(8) 4552-4557. Thus, one skilled in the art could generate a large number of nucleotide and/or polypeptide variants having, for example, at least 95-99% identity to the reference sequence described herein and screen such for desired phenotypes according to methods routine in the art.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

Generally, conservative substitutions can be made at any position so long as the required activity is retained. So-called conservative exchanges can be carried out in which the amino acid which is replaced has a similar property as the original amino acid, for example the exchange of Glu by Asp, Gln by Asn, Val by Ile, Leu by Ile, and Ser by Thr. For example, amino acids with similar properties can be Aliphatic amino acids (e.g., Glycine, Alanine, Valine, Leucine, Isoleucine); Hydroxyl or sulfur/selenium-containing amino acids (e.g., Serine, Cysteine, Selenocysteine, Threonine, Methionine); Cyclic amino acids (e.g., Proline); Aromatic amino acids (e.g., Phenylalanine, Tyrosine, Tryptophan); Basic amino acids (e.g., Histidine, Lysine, Arginine); or Acidic and their Amide (e.g., Aspartate, Glutamate, Asparagine, Glutamine). Deletion is the replacement of an amino acid by a direct bond. Positions for deletions include the termini of a polypeptide and linkages between individual protein domains. Insertions are introductions of amino acids into the polypeptide chain, a direct bond formally being replaced by one or more amino acids. Amino acid sequence can be modulated with the help of art-known computer simulation programs that can produce a polypeptide with, for example, improved activity or altered regulation. On the basis of this artificially generated polypeptide sequences, a corresponding nucleic acid molecule coding for such a modulated polypeptide can be synthesized in-vitro using the specific codon-usage of the desired host cell.

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature ($T_m$) of a DNA duplex between the two sequences. If a particular duplex has a melting temperature lower than 65° C. in the salt conditions of a 6×SSC, then the two sequences will not hybridize. On the other hand, if the melting temperature is above 65° C. in the same salt conditions, then the sequences will hybridize. In general, the melting temperature for any hybridized DNA:DNA sequence can be determined using the following formula: $T_m$=81.5° C.+16.6($\log_{10}$[Na$^+$])+0.41(fraction G/C content)−0.63(% formamide)−(600/l). Furthermore, the $T_m$ of a DNA: DNA hybrid is decreased by 1-1.5° C. for every 1% decrease in nucleotide identity (see e.g., Sambrook and Russel, 2006).

Host cells can be transformed using a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754). Such techniques include, but are not limited to, viral infection, calcium phosphate transfection, liposome-mediated transfection, microprojectile-mediated delivery, receptor-mediated uptake, cell fusion, electroporation, and the like. The transfected cells can be selected and propagated to provide recombinant host cells that comprise the expression vector stably integrated in the host cell genome.

| Conservative Substitutions I | |
|---|---|
| Side Chain Characteristic | Amino Acid |
| Aliphatic Non-polar | G A P I L V |
| Polar-uncharged | C S T M N Q |
| Polar-charged | D E K R |
| Aromatic | H F WY |
| Other | N Q D E |

| Conservative Substitutions II | |
|---|---|
| Side Chain Characteristic | Amino Acid |
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

| Conservative Substitutions III | |
|---|---|
| Original Residue | Exemplary Substitution |
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr, Phe |
| Tyr (Y) | Trp, Phe, Tur, Ser |
| Val (V) | Ile, Leu, Met, Phe, Ala |

Exemplary nucleic acids which may be introduced to a host cell include, for example, DNA sequences or genes from another species, or even genes or sequences which originate with or are present in the same species, but are incorporated into recipient cells by genetic engineering methods. The term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the cell, DNA from another individual of the same type of organism, DNA from a different organism, or a DNA generated externally, such as a DNA sequence containing an antisense message of a gene, or a DNA sequence encoding a synthetic or modified version of a gene.

Host strains developed according to the approaches described herein can be evaluated by a number of means known in the art (see e.g., Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Methods of down-regulation or silencing genes are known in the art. For example, expressed protein activity can be down-regulated or eliminated using antisense oligonucleotides, protein aptamers, nucleotide aptamers, and RNA interference (RNAi) (e.g., small interfering RNAs (siRNA), short hairpin RNA (shRNA), and micro RNAs (miRNA) (see e.g., Fanning and Symonds (2006) Handb Exp Pharmacol. 173, 289-303G, describing hammerhead ribozymes and small hairpin RNA; Helene, C., et al. (1992) Ann. N.Y. Acad. Sci. 660, 27-36; Maher (1992) Bioassays 14(12): 807-15, describing targeting deoxyribonucleotide sequences; Lee et al. (2006) Curr Opin Chem Biol. 10, 1-8, describing aptamers; Reynolds et al. (2004) Nature Biotechnology 22(3), 326-330, describing RNAi; Pushparaj and Melendez (2006) Clinical and Experimental Pharmacology and Physiology 33(5-6), 504-510, describing RNAi; Dillon et al. (2005) Annual Review of Physiology 67, 147-173, describing RNAi; Dykxhoorn and Lieberman (2005) Annual Review of Medicine 56, 401-423, describing RNAi). RNAi molecules are commercially available from a variety of sources (e.g., Ambion, TX; Sigma Aldrich, MO; Invitrogen). Several siRNA molecule design programs using a variety of algorithms are known to the art (see e.g., Cenix algorithm, Ambion; BLOCK-iT™ RNAi Designer, Invitrogen; siRNA Whitehead Institute Design Tools, Bioinofrmatics & Research Computing). Traits influential in defining optimal siRNA sequences include G/C content at the termini of the siRNAs, Tm of specific internal domains of the siRNA, siRNA length, position of the target sequence within the CDS (coding region), and nucleotide content of the 3' overhangs.

As will be appreciated based upon the foregoing specification, the above-described aspects of the disclosure may be implemented using computer programming or engineering techniques including computer software, firmware, hardware, or any combination or subset thereof. Any such resulting program, having computer-readable code means, may be embodied or provided within one or more computer-readable media, thereby making a computer program product, i.e., an article of manufacture, according to the discussed aspects of the disclosure. The computer-readable media may be, for example, but is not limited to, a fixed (hard) drive, diskette, optical disk, magnetic tape, semiconductor memory such as read-only memory (ROM), and/or any transmitting/receiving media, such as the Internet or other communication network or link. The article of manufacture containing the computer code may be made and/or used by executing the code directly from one medium, by copying the code from one medium to another medium, or by transmitting the code over a network.

These computer programs (also known as programs, software, software applications, "apps", or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The "machine-readable medium" and "computer-readable medium," however, do not include transitory signals. The term "machine-readable signal" refers to any signal used to provide machine instructions and/or data to a programmable processor.

As used herein, a processor may include any programmable system including systems using micro-controllers, reduced instruction set circuits (RISC), application specific integrated circuits (ASICs), logic circuits, and any other circuit or processor capable of executing the functions described herein. The above examples are examples only, and are thus not intended to limit in any way the definition and/or meaning of the term "processor."

As used herein, the terms "software" and "firmware" are interchangeable and include any computer program stored in memory for execution by a processor, including RAM memory, ROM memory, EPROM memory, EEPROM memory, and non-volatile RAM (NVRAM) memory. The above memory types are examples only and are thus not limiting as to the types of memory usable for the storage of a computer program.

In one aspect, a computer program is provided, and the program is embodied on a computer readable medium. In one aspect, the system is executed on a single computer system, without requiring a connection to a server computer. In a further aspect, the system is being run in a Windows® environment (Windows is a registered trademark of Microsoft Corporation, Redmond, Washington). In yet another aspect, the system is run on a mainframe environment and a UNIX® server environment (UNIX is a registered trademark of X/Open Company Limited located in Reading, Berkshire, United Kingdom). The application is flexible and designed to run in various different environments without compromising any major functionality.

In some aspects, the system includes multiple components distributed among a plurality of computing devices. One or more components may be in the form of computer-executable instructions embodied in a computer-readable medium. The systems and processes are not limited to the specific aspects described herein. In addition, components of each system and each process can be practiced independent and separate from other components and processes described herein. Each component and process can also be used in combination with other assembly packages and processes. The present aspects may enhance the functionality and functioning of computers and/or computer systems.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1

Detection of Tumor-Derived Copy Number Alterations in NF1 Patients Using ULP-WGS To assess whether alterations in tumor-derived genomic copy-number alterations in Neurofibromatosis Type 1(NF1) patients are detectable in cell-free plasma DNA using ultra-low-pass whole genome sequencing (ULP-WGS), the following experiments were conducted. In addition, to determine whether the tumor-derived genomic copy-number alterations were able to distinguish patients with MPNST from those with benign plexiform neurofibroma, the following experiments were conducted.

Blood samples were collected using EDTA tubes from NF1 patients with MPNST (n=9) or benign plexiform neurofibroma (n=15). Plasma was immediately separated, and DNA was isolated from plasma volumes ranging from 2-8 mL using the QiaAMP Circulating Nucleic Acids Kit (Qiagen). Libraries were prepared with between 10-50 ng cell-free DNA using the KAPA HyperPrep kit (Roche). After Agilent Bioanalyzer analysis, libraries were sequenced on an Illumina Hiseq X10. Reads were aligned with BWA-MEM v7.16 and copy number changes were quantified using CNVkit v0.9. Genome-wide segmental copy number changes were evaluated in regions>1 Mb. Copy number alterations were considered significant if log 2 fold-change was >|0.05|.

Across all samples, median sequencing depth was 1.4× (range 0.7×-1.9×). For samples reaching median depth>1.0×, segmental copy number alterations (regions>1 Mb) were observed in all MPNST patient samples (8/8) and no benign plexiform patients (0/13) (Fisher's exact test P<0.0001). Additionally, in a subset of MPNST cases (3/9), focal copy number loss was observed in SUZ12, a variant that has been associated with MPNST transformation.

The results of these experiments determined that liquid biopsy cell-free DNA analysis by ULP-WGS effectively distinguished NF1 patients with MPNST from those with only benign plexiform neurofibroma, suggesting this method could have clinical utility to sensitively detect malignant transformation in this high-risk patient population.

Example 2

Development of Hybrid Capture Gene Panel to Differentiate MPNST from Benign PN

To develop a hybrid capture gene panel configured to differentiate MPNST from benign PN conditions based on cfDNA obtained non-invasively from patient plasma samples, the following experiments were conducted.

Figure 2:
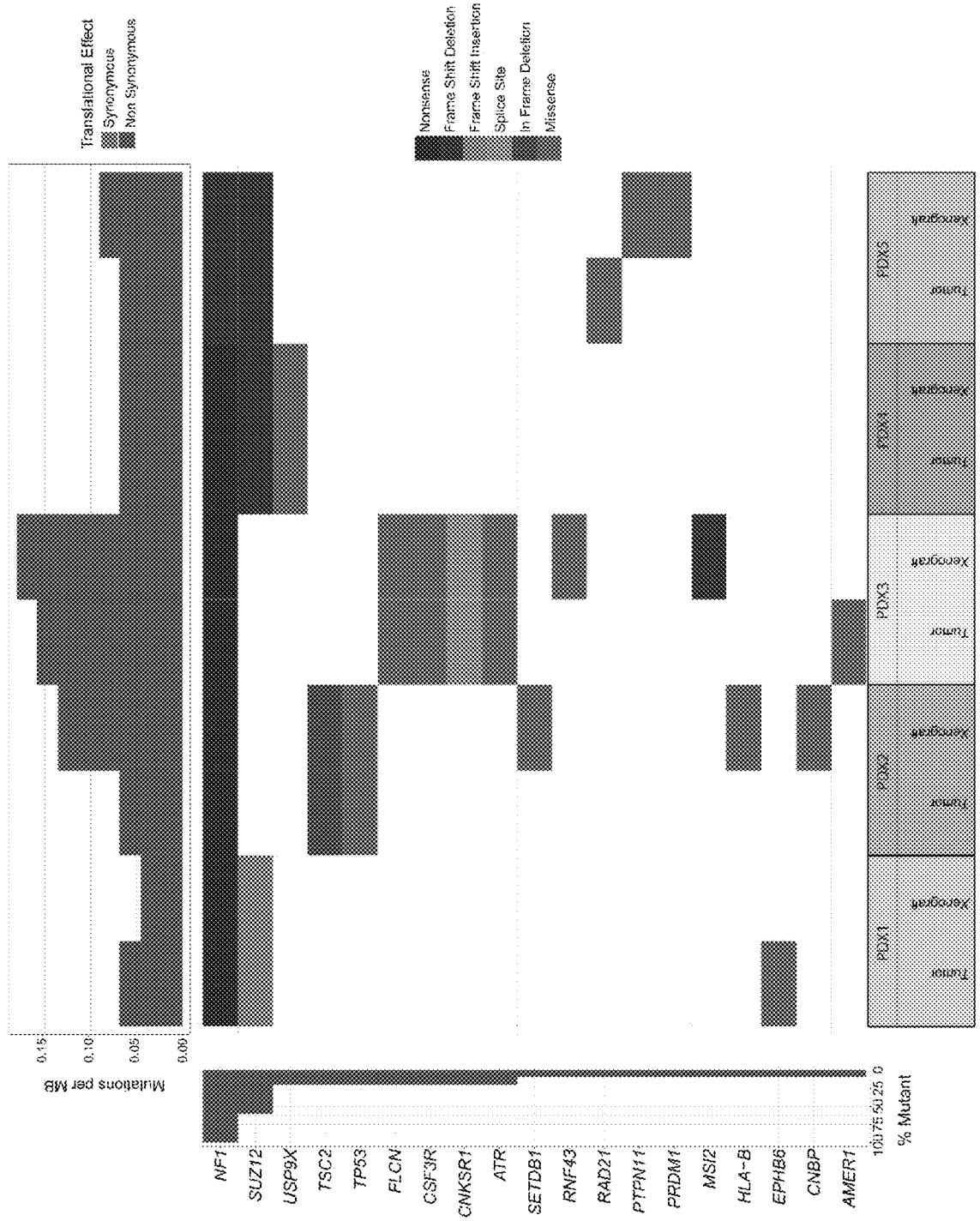
FIG. 2 is a map of SNVs and indels identified in MPNST cases and corresponding PDX lines. Whole exome sequencing identified somatic mutations in NF1, SUZ12 and TP53, known drivers for MPNST progression along with several other SNVs/indels.

To identify MPNST-associated genomic alterations, xenograft (PDX) lines were developed from patient tissue samples and comprehensive genomic and histologic analyses were performed five of these PDX lines. Through these genomic analyses, we identified mutations characteristic of MPNST. As expected, all MPNSTs and corresponding PDX lines demonstrate mutations in NF1. Given that this is the driver for initial tumor formation in NF1, mutations in NF1 will be present in both the PN and the MPNST and as such cannot be used to distinguish these entities. We also observed SNVs and indels in SUZ12 and TP53 at a high variant allele frequency (VAF) in multiple MPNST cases. This is in line with the literature and our prior work, which supports these genes as playing a role in MPNST progression. Mutations in these genes are not seen in PN. In the waterfall plot in FIG. 2, several other genes were identified as being mutated at lower VAFs in some MPNST cases. Thus, a targeted capture panel may be designed to include all these genes which are shown to be mutated in NF1.

Figure 3:
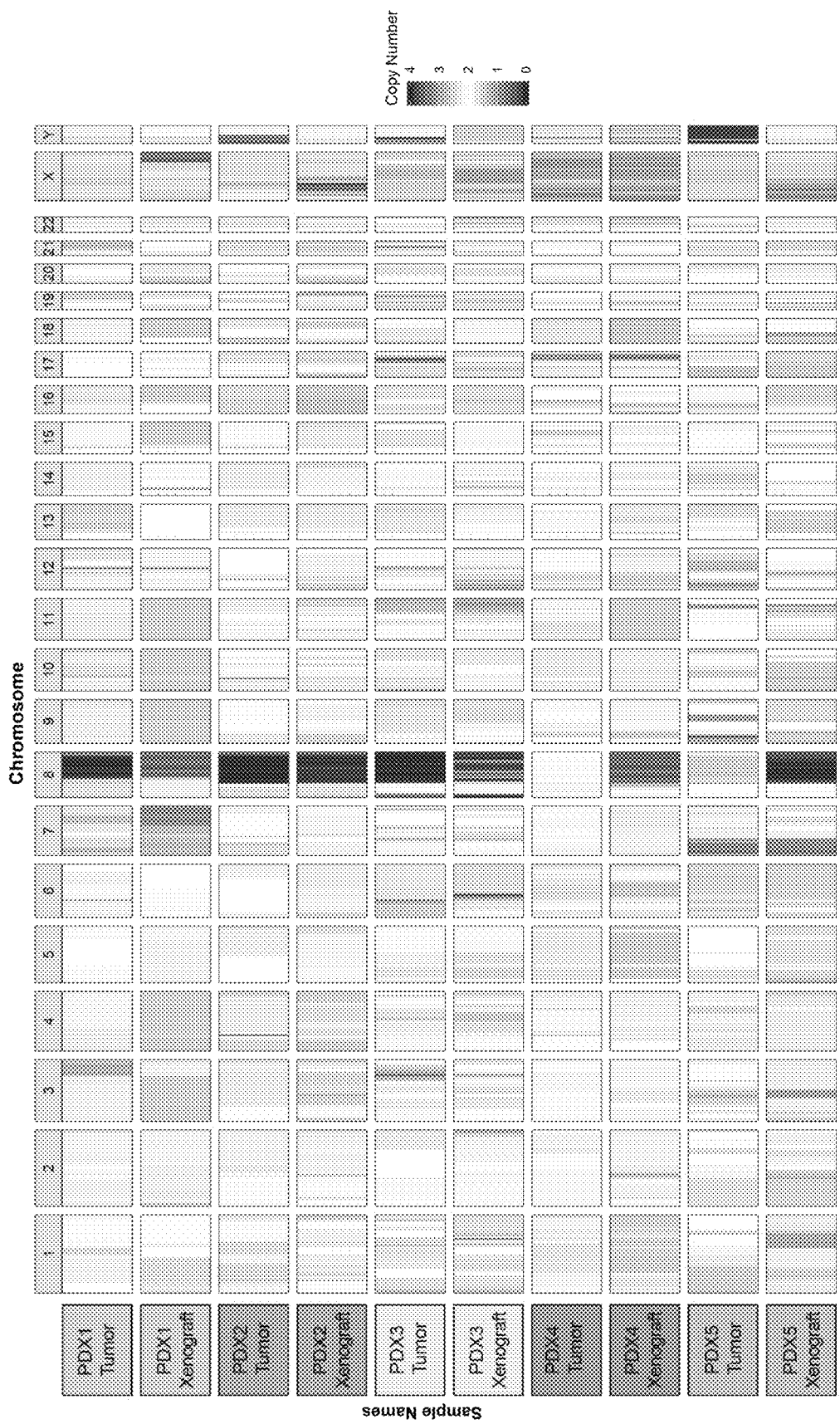
FIG. 3 is a heat map summarizing copy number alterations across MPNST patients as well as each corresponding PDX. Genome-wide copy number analysis comparing tumors and their xenografts. Deletions are colored in blue and amplifications in red. Particularly notable is the stereotypic amplification of a large region of chromosome 8. Sequencing at 100× depth.
Figure 4:
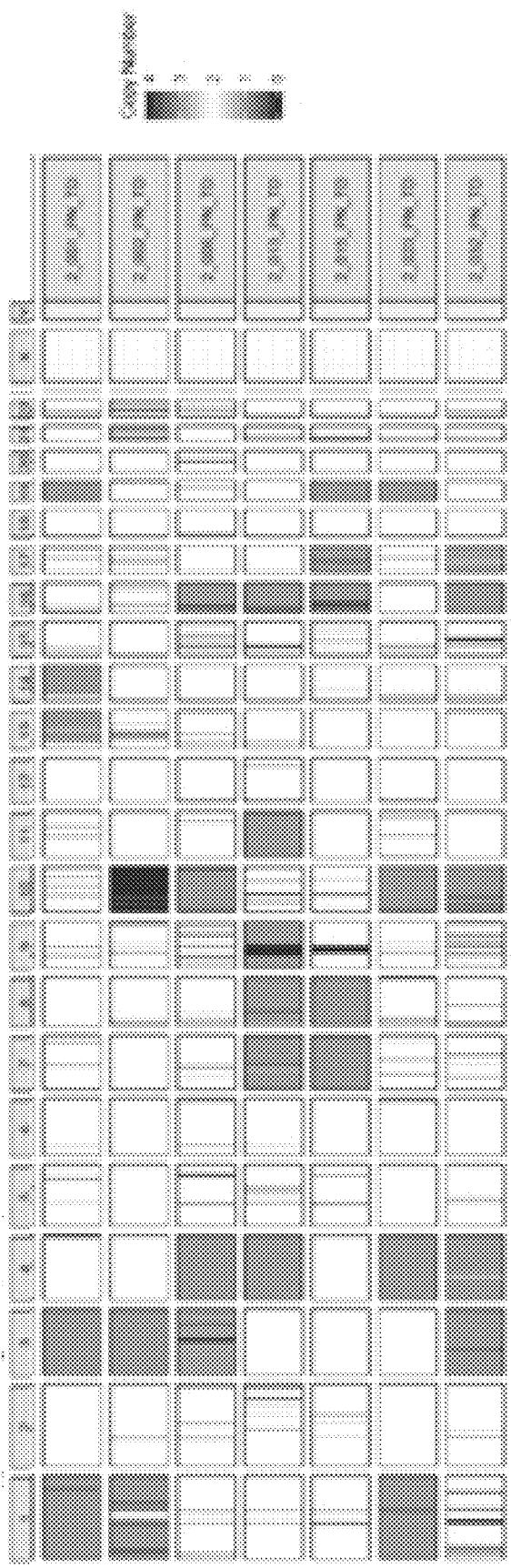
FIG. 4 is a map of copy number alterations across PN patients. Genome-wide copy number analysis examining tumors from benign PN tumors. Deletions are colored in blue and amplifications in red. Particularly notable is the finding that these tumors are relatively copy number neutral compared to MPNSTs. Sequencing at 100× depth.
Figure 5A:
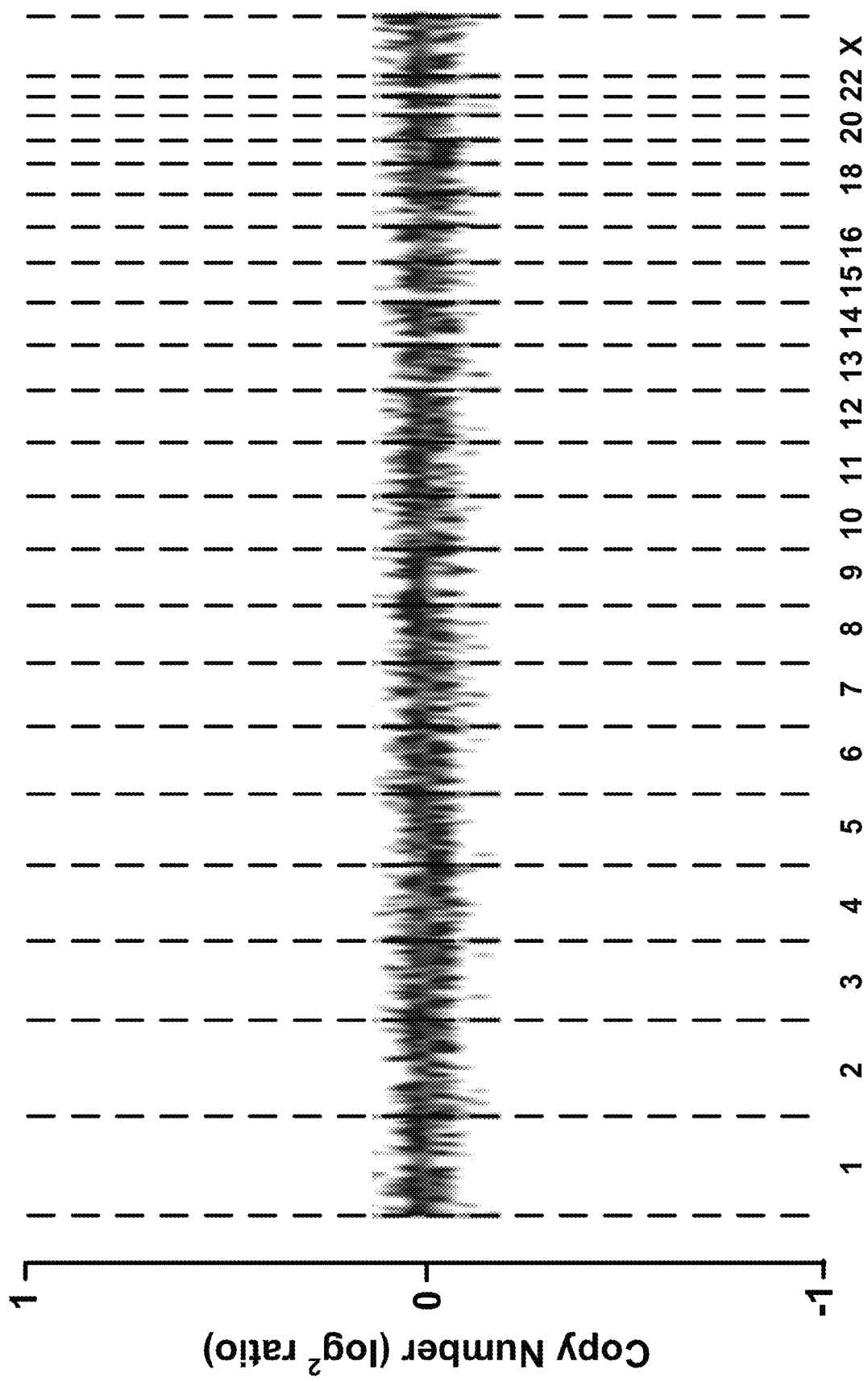
FIG. 5A is a graph summarizing the results of low-pass whole genome sequencing (~1×) performed on plasma taken from an NF1 patient benign PN, showing uniformly diploid genes.
Figure 5B:
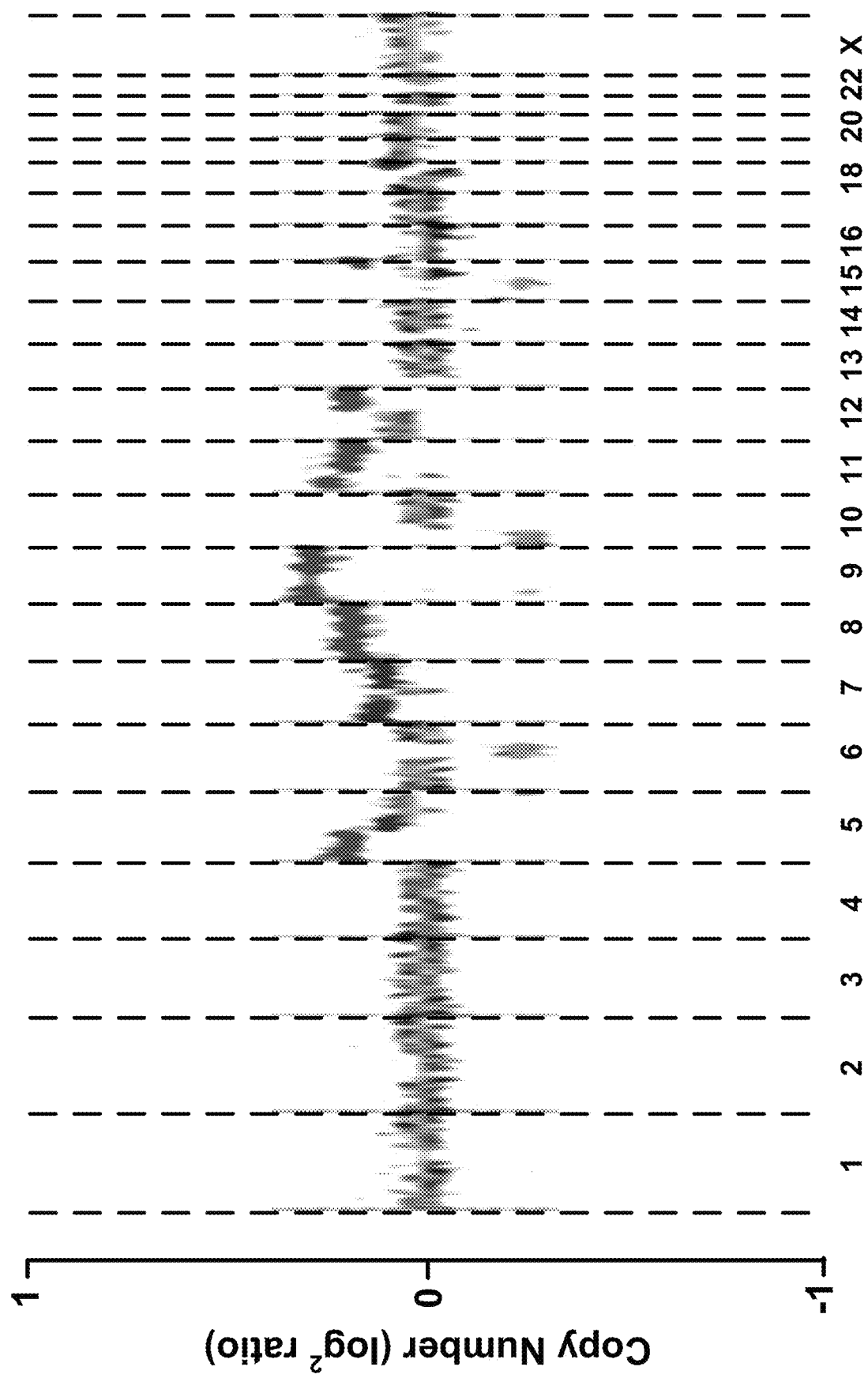
FIG. 5B is a graph summarizing the results of low-pass whole genome sequencing (~1×) performed on plasma taken from an NF1 patient with MPNST, showing detectable aneuploidy with copy number amplification of chromosomes 8, 9, 11, 5p and 12q.

Through copy number analysis performed to identify other potential drivers of MPNST progression, we also identified a large area of chromosome 8 that is amplified in all MPNST and corresponding PDX samples (FIG. 3). Given this intriguing finding, we interrogated prior sequencing data on PNs to see if this area is amplified in PN as well. We observed that PNs are relatively quiet in terms of copy number changes when compared to MPNSTs. Additionally, no amplification of chromosome 8 was observed in PNs (FIG. 4). Thus to interrogate this copy number alteration that appears specific to MPNST, following targeted hybrid capture NGS of plasma-derived cell-free DNA with a median de-duplicated depth of ~2000× to interrogate SNVs and indels, we will perform low-pass whole genome sequencing using the sequencing reads that were off-target from the capture panel (~50% of total reads) which provides ~0.2× low-pass whole genome coverage. In a small pilot, we demonstrated the ability to detect copy number changes by low pass whole genome sequencing on cell-free DNA from the plasma of one PN (FIG. 5A) and one patient with MPNST (FIG. 5B).

The combined assay of hybrid capture based NGS (using on-target reads) and low-pass whole genome sequencing (using off-target reads) will enable us to non-invasively distinguish MPNST patients from healthy controls, and recapitulate previous invasive tumor sequencing results.

Example 3

Assessment of CNV in MPNST Using WGS of cfDNA in Plasma Samples

To assess copy number variations associated with MPNST base on whole genome sequencing of cell-free DNA from plasma samples, the following experiments were conducted.

Figure 6:
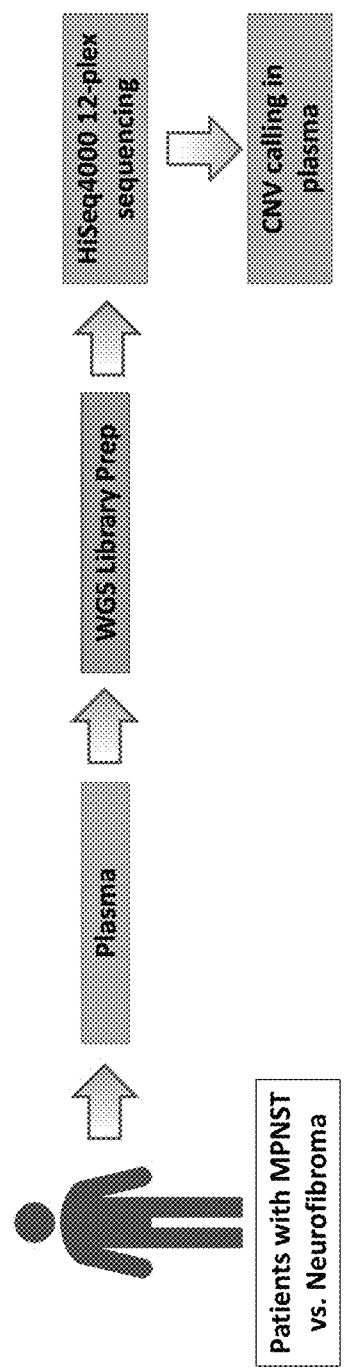
FIG. 6 is a flow chart summarizing a process of sequencing NF and MPNST patients following definitive-intent surgery as typically follows neoadjuvant chemo.

Next Generation Sequencing (NGS) and circulating tumor DNA (ctDNA) analysis were conducted as summarized in FIG. 6. ~20 mL of blood was collected using EDTA blood collection tubes from 5 patients with a diagnosis of advanced-stage MPNST and from 5 healthy volunteers to serve as a comparative control. After centrifugation at 1800×g for 10 minutes, plasma was removed using filtertips, then spun a second time at 1800×g for 10 minutes (to reduce the risk of genomic DNA contamination of cell-free DNA), frozen at −80° C., then stored in liquid nitrogen. A 1 mL aliquot of the remaining plasma-depleted whole blood (from the initial spin) was also frozen and stored for germline DNA extraction.

Purified plasma was thawed at room temperature, and cfDNA was extracted from 2 to 8 mL of plasma using the QIAamp Circulating Nucleic Acid kit (Qiagen, Hilden, Germany). Extracted DNA concentration was measured using the Qubit dsDNA High-Sensitivity assay (ThermoFisher, Waltham, Massachusetts), and cfDNA concentration and quality were assessed using a Bioanalyzer (Agilent Technologies, Santa Clara, California) or Tapestation (Agilent Technologies, Santa Clara, California). Isolated cfDNA was stored at −20° C. until library preparation.

Figure 7:
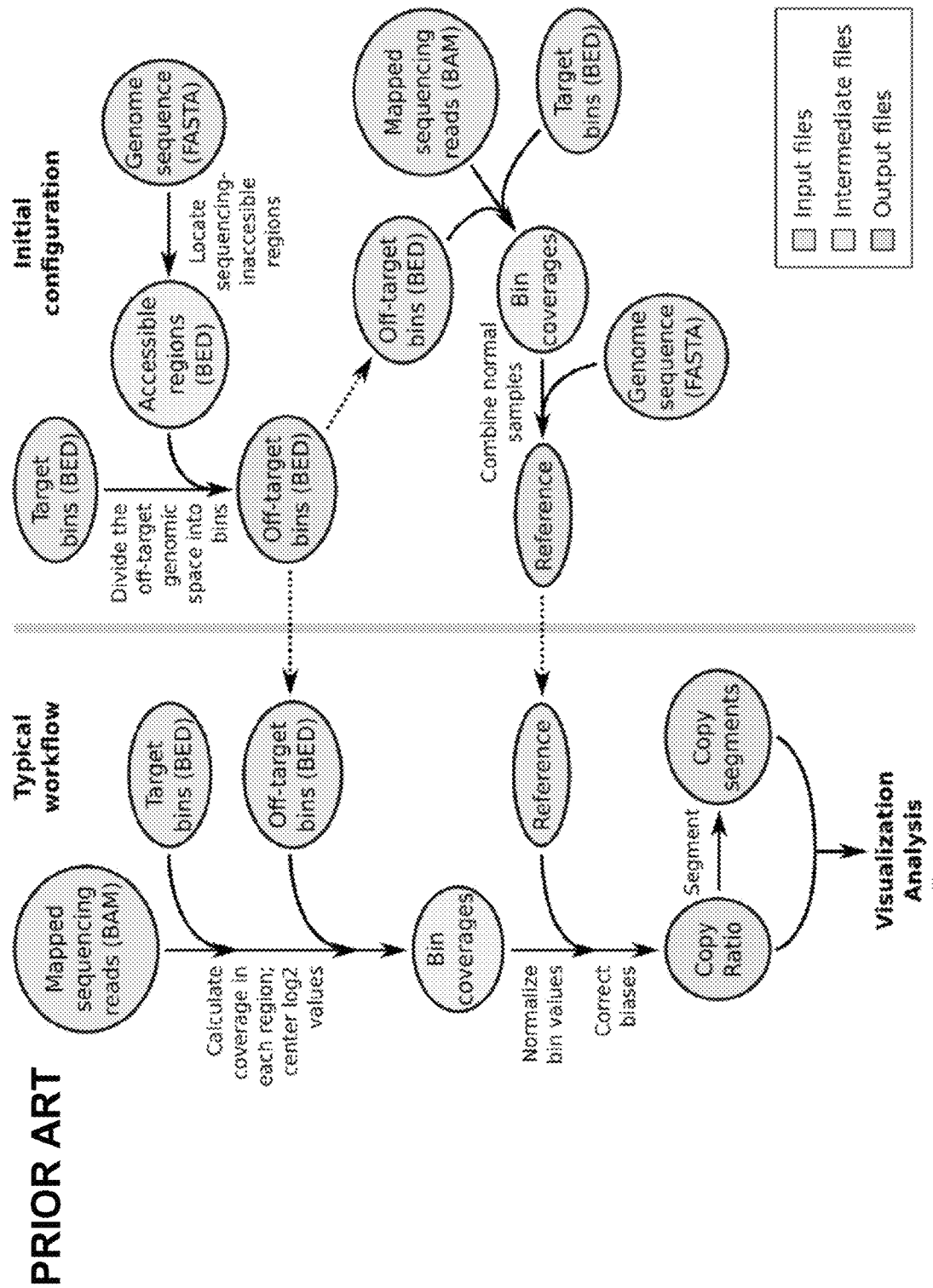
FIG. 7 is a flow chart illustrating a representative workflow used to develop a hybrid capture panel used to obtain targeted NGS data.

Sequencing libraries were constructed from cfDNA (5-60 ng) using commercial kits per the manufacturers' instructions: TruSeq Nano (Illumina, San Diego, California). Constructed libraries were balanced, pooled, and sequenced using 150 bp paired-end reads on a HiSeq 4000 (Illumina, San Diego, California). Data were then quality filtered and pooled for analysis. FIG. 7 is a flow chart illustrating a representative workflow for the analysis of the sequenced cfDNA reads.

Figure 8A:
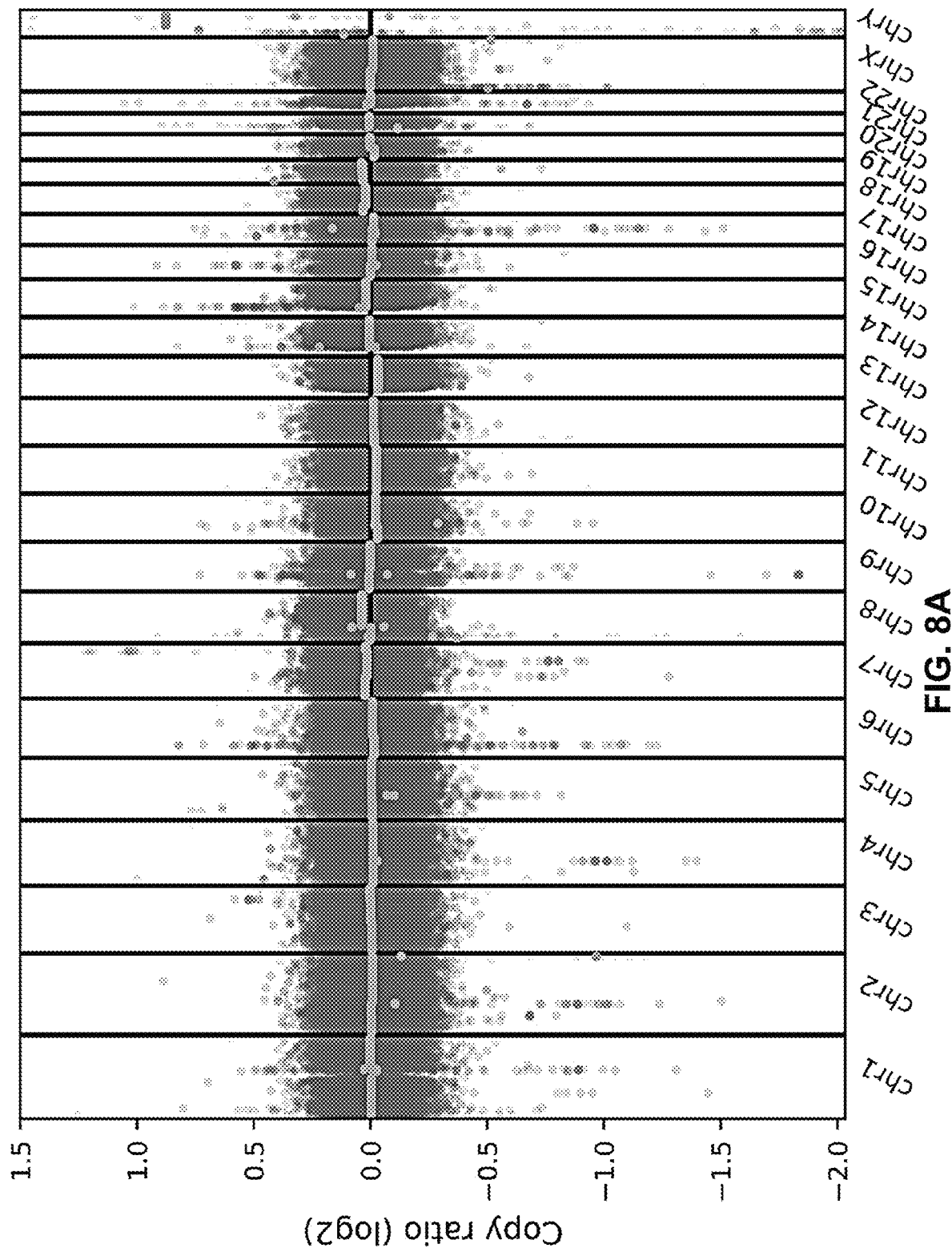
FIG. 8A is a graph summarizing the results of low-pass whole genome sequencing (~1×) performed on plasma taken from an NF1 patient MPNST showing detectable aneuploidy with copy number amplification of chromosome 8.
Figure 8B:
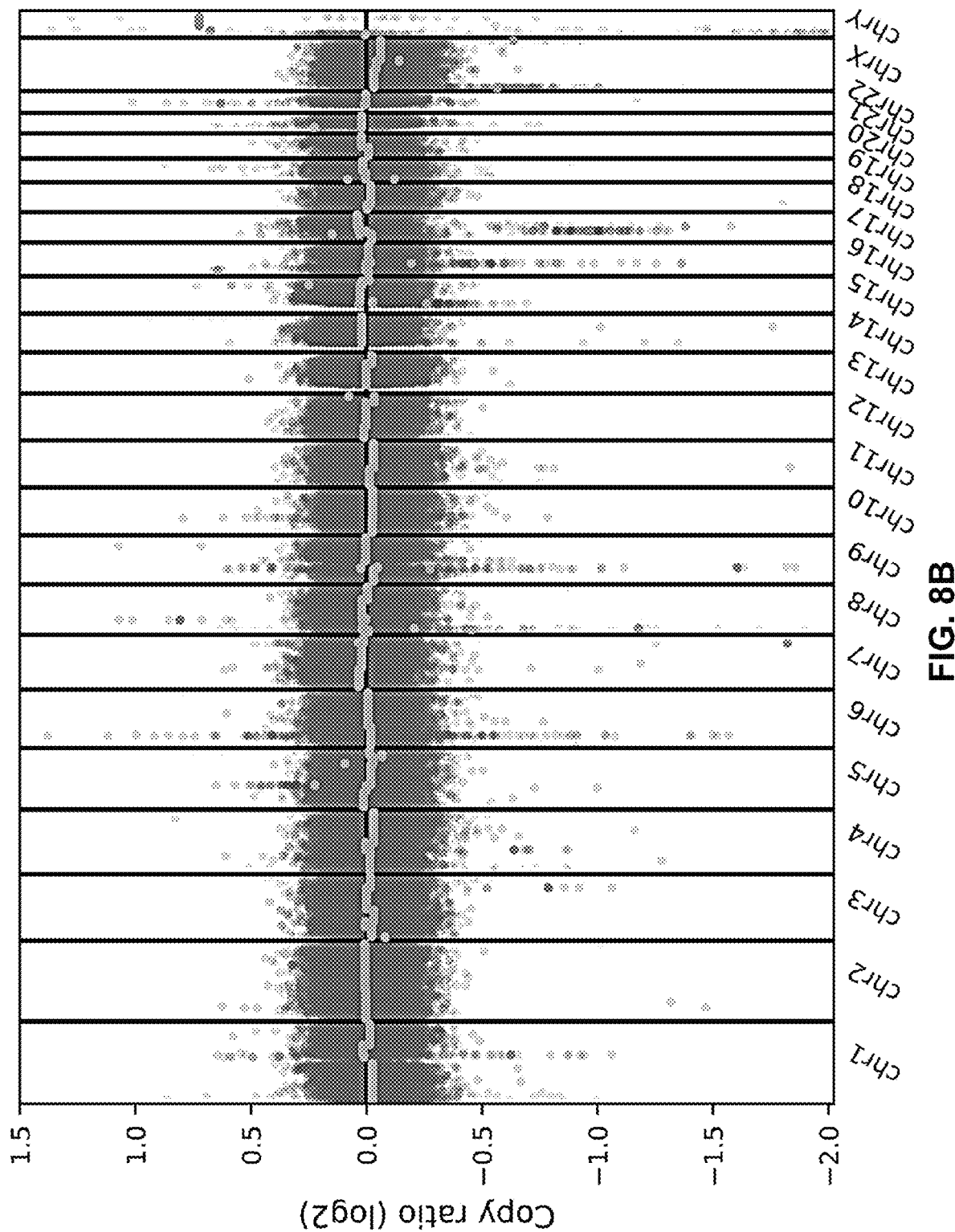
FIG. 8B is a graph summarizing the results of low-pass whole genome sequencing (~1×) performed on plasma taken from an NF1 patient with MPNST showing detectable aneuploidy.
Figure 8C:
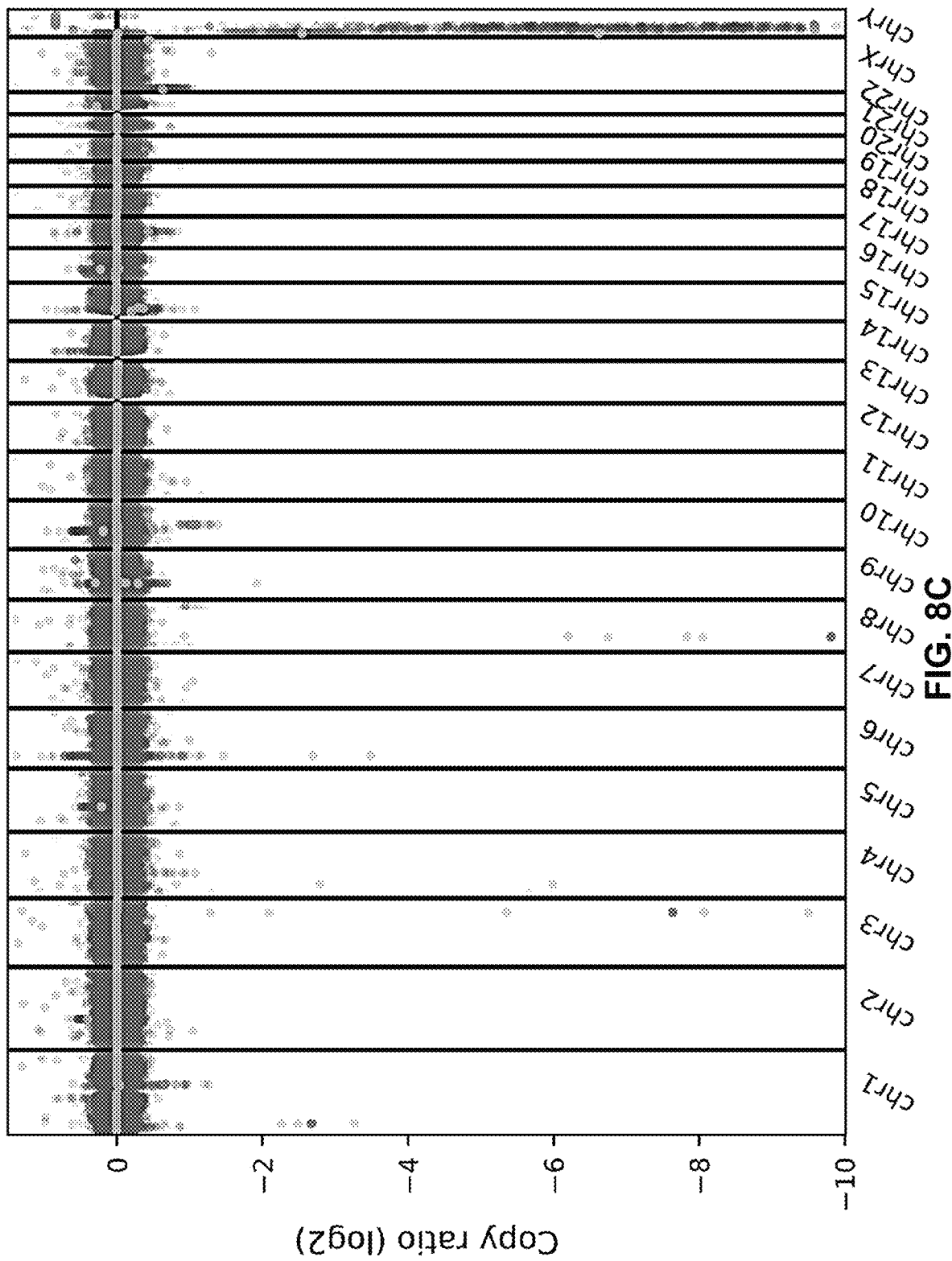
FIG. 8C is a graph summarizing the results of low-pass whole genome sequencing (~1×) performed on plasma taken from an NF1 patient with atypical neurofibroma showing minimal detectable aneuploidy.

Visualization of genome-wide CNAs at specific loci was generated from compiled log 2 ratios of copy number for all study plasma specimens. Reads were classified as copy number gain if log 2 of the copy number ratio was >0.58 (log 2 (3/2)) and loss if log 2 of the copy number ratio was <−1.0 (log 2 (1/2)). Bin CNA plots (FIGS. 8A, 8B, and 8C) reflect copy number changes from baseline in the tumor-only fraction of each sample. FIGS. 8A and 8B correspond to NF1 patients with MPNST showing detectable aneuploidy. FIG. 8C corresponds to an NF1 patient with atypical neurofibroma showing minimal detectable aneuploidy.

The results of these experiments demonstrated that the whole genome sequencing was able to detect copy number variations associated with MPNST and not NF1 patients.

Example 4

Noninvasive Differentiation of MPNST from Benign PN Based on cfDNA Fragment Size Distributions and Genomic Copy Number Alterations in Plasma Samples To develop and assess a method for differentiating MPNST from benign PN based on the analysis and quantification of copy number alterations (CNAs) and cfDNA fragment size distributions in blood plasma, the following experiments were conducted.

Figure 9:
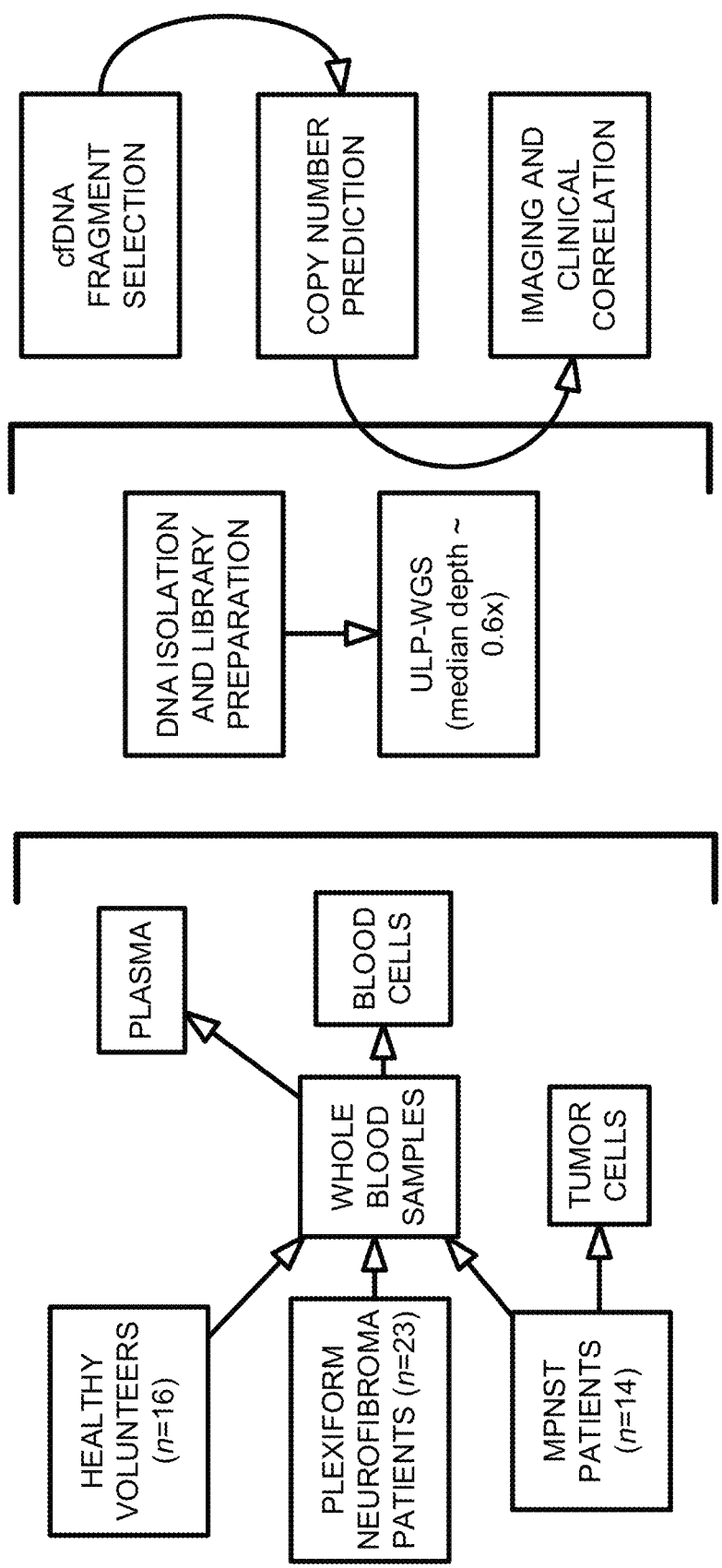
FIG. 9 is a flow chart illustrating the development of a method of predicting the development of MPNST in a patient based on ULP-WGS sequencing and analysis of cfDNA.

Blood samples were prospectively collected from NF1 patients with MPNST and PN tumors with the aim of distinguishing these different tumor types by plasma cfDNA analysis (FIG. 9). Patients from two treatment centers with clinically and radiographically diagnosed PN or biopsyproven MPNST were enrolled onto this multi-institutional cross-sectional study with written informed consent. NF1 status was determined clinically by consensus criteria. Five participants with MPNST who did not meet NF1 consensus criteria were also included in the analysis. A total of 14 MPNST and 23 PN patients were enrolled with peripheral blood collected at the time of enrollment. MPNST patients had serial plasma samples collected for a total of 46 MPNST plasma samples (average 3, maximum 6 per participant). When available, tissue was also collected at a single time point (n=4 participants). When peripheral blood mononuclear cells (PBMCs) were isolated from whole blood, these were sequenced as germline DNA (n=16 participants). All patients under-went clinical management and follow-up by board-certified physicians per the standard-of-care.

To quantify CNAs, we profiled 105 biospecimens including 85 plasma samples from 53 participants by ULP-WGS downsampled to 10 million paired reads (approximately 0.6× genome-wide cover-age) (FIG. 9). Participant groups compared were MPNST and PN patients as well as healthy donor controls. Specimen types included blood plasma cfDNA, blood leukocyte germ-line DNA, and frozen tumor specimens. The median age was 36, 27, and 32.5 for MPNST patients, PN patients, and healthy donors, respectively. Exclusion criteria included diagnosis of a non-MPNST malignancy. No PN patients developed any clinical or radiographic evidence of MPNST transformation during a median study follow-up time of nearly 2 years (median 690 days; interquartile range (IQR) of 531 to 1,140 days). For 2 participants, sar015 and sar037, large PN resection was performed for lesion-related morbidity with final pathology confirming the PN diagnosis. Among patients with MPNST, 86.7% received chemotherapy, 35.7% received radiotherapy, and 42.9% underwent surgical resection.

Healthy Controls

Healthy donor blood samples were obtained at a single time point from appropriately consented donors. Eligibility for healthy controls included age greater than 18 years old and no known history of neoplastic or hematological disorders.

Clinical Specimens

Serial peripheral blood samples were collected throughout the clinical course for consenting MPNST patients or at a single time point for PN patients. Treatment regimen for MPNST was determined by the primary treating clinicians and included radiotherapy, surgery, and cytotoxic chemotherapy.

Venous blood samples (10 to 30 mL) were collected in EDTA (BD Biosciences, San Jose, California) or Cell-Free DNA BCT (Streck Laboratories, La Vista, Nebraska) tubes. EDTA tubes were processed within 4 hours of collection, while Cell-Free DNA BCT tubes were processed within 7 days of collection. Whole blood samples were centrifuged at room temperature (1200-1900×g for 10 minutes). Isolated plasma was centrifuged a second time at room temperature (1800-15,000×g for 10 minutes) in low-bind Eppendorf tubes to remove residual cells. Purified plasma was frozen at −80° C. until cfDNA isolation.

Plasma Cell-Free DNA Isolation

Purified plasma was thawed at room temperature, and cfDNA was extracted from 2 to 8 mL of plasma using the QIAamp Circulating Nucleic Acid kit (Qiagen, Hilden, Germany). Extracted DNA concentration was measured using the Qubit dsDNA High-Sensitivity assay (Thermo-Fisher, Waltham, Massachusetts), and cfDNA concentration and quality were assessed using a Bioanalyzer (Agilent Technologies, Santa Clara, California) or Tapestation (Agilent Technologies, Santa Clara, California). Isolated cfDNA was stored at −20° C. until library preparation.

Germline DNA Isolation and Processing

After centrifuging clinical venous blood samples and removing plasma supernatant per above, the red blood cells and buffy coat were resuspended in PBS for germline DNA extraction using the DNeasy Blood and Tissue kit (Qiagen, Hilden, Germany). For a subset of samples, germ-line DNA from PBMCs was collected in and extracted using PAXgene Blood DNA tubes and kit (PreAnalytix, Germantown, Maryland). DNA was stored at −20° C. until further processing. Germline DNA was then fragmented using a LE220 focused ultrasonicator (Covaris, Woburn, Massachusetts) or a Q800R3 sonicator (Qsonica LLC, Newtown, Connecticut) according to the manufacturer's instructions and previously published methods to a target length of 200 bp. DNA lengths were assessed using a Bioanalyzer (Agilent Technologies, Santa Clara, California).

Tumor DNA Isolation and Processing

Tumor tissue was not procured for research unless clinically indicated and available following the standard clinical pathology workflow. When available, tumor tissue was snap-frozen and stored at −80° C. or stored in formalin-fixed paraffin-embedding (FFPE). Nucleic acids were isolated from tumor FFPE samples using the manufacturer's protocol with the AllPrep DNA/RNA FFPE kit (Qiagen, Hilden, Germany). DNA was extracted from snap-frozen tumor tissue samples using the DNeasy Blood and Tissue kit (Qiagen, Hilden, Germany). Extracted DNA was stored at −20° C. until further processing. Tissue DNA was subsequently fragmented using a LE220 focused ultrasonicator (Covaris, Woburn, Massachusetts) or Q800R3 sonicator (Qso-nica LLC, Newtown, Connecticut) and analyzed using a Bioanalyzer (Agilent Technologies, Santa Clara, California) as described above.

DNA Library Construction and Sequencing

Sequencing libraries were constructed from cfDNA (5-60 ng) or germline/tumor DNA (32-100 ng) using commercial kits per the manufacturers' instructions: TruSeq Nano (Illumina, San Diego, California) or Kapa HyperPrep (Roche, Basel, Switzerland). Constructed libraries were balanced, pooled, and sequenced using 150 bp paired-end reads on a NovaSeq (Illumina, San Diego, California) or HiSeq 4000 (Illumina, San Diego, California). Data were then quality filtered and pooled for analysis.

Copy Number Alteration and Tumor Fraction Analysis

Sequencing data were demultiplexed, and raw reads were quality filtered using fastp v.0.2. Quality-filtered reads were then aligned to the hg19 human genome assembly using BWA v.0.7.17. Aligned reads were deduplicated with Samtools v.1.7, then downsampled to 10 million read pairs (WGS coverage approximately 0.6×), or separately for comparison purposes to 5 million read pairs (WGS coverage approximately 0.3×). Genomic coverage was estimated using MosDepth. To enrich for circulating tumor DNA (ctDNA) fragments, in silico size selection was applied to all cfDNA samples. Only quality-filtered reads between fragment lengths of 90 and 150 bp were considered for copy number and tumor fraction analysis for cfDNA samples, while such size selection was not performed for tumor and germline samples. GC content and mappability bias correction, depth-based local copy number estimates, and copy number-based estimation of tumor fraction were then performed using the ichorCNA tool (Broad v.0.2.0). Briefly, reads were summed in nonoverlapping windows of 106 bases; local read depth was corrected for GC bias and known regions of low mappability, and artifacts were removed by comparison to ichorCNA's built-in healthy control reference. CNAs were predicted using recommended low tumor fraction parameters for cfDNA samples and default parameters for tumor and germline samples. X and Y chromosomes were not considered in copy number ratios. ichorCNA then used these binned, bias-corrected copy number values to model a two-component mixture of tumor-derived and nontumor-derived fragments, from which it inferred the fraction of reads in each sample originating from tumor (tumor fraction). Both copy number state and tumor fraction were determined by ichorCNA.

Fragment Size Analysis

Following the sequencing quality control, deduplication, alignment, and downsampling steps described above, read-pair fragment sizes for cfDNA samples were calculated using deepTools bamPEFragmentSize. The distribution of each sample's fragment sizes was estimated by kernel density. cfDNA fragment size distributions were compared between the 3 clinical states (healthy control, PN, and MPNST) and between high and low tumor fraction samples by two-sided Kolmogorov-Smirnov testing.

Power and Statistical Analyses

Previous tissue-based studies have shown that PN harbor few genome-wide CNAs but acquire significant genomic instability during malignant transformation to MPNST. Based on these known significant CNA differences between MPNST and PN tumors, we assumed a large effect size would also be evident comparing MPNST plasma tumor fraction to plasma from PN patients or healthy controls. Using Cohen's f=0.6 with an α=0.05 and power=0.80, we projected that the sample size needed to detect differences between these 3 categories would be n=10 per group. The category group sizes described above met or exceeded this estimate for all comparisons.

When testing associations between plasma tumor fraction and clinical status (FIGS. 12A, 12B, and 12C), we limited MPNST plasma samples to those collected either prior to all treatments or after a wash-out period of at least 21 days after completion of chemotherapy or radiotherapy (designated as pretreatment or baseline MPNST samples, respectively). The distributions of plasma tumor fractions for each clinical status were compared by Kruskal-Wallis H test with pairwise comparisons by Dunn test. To further compare pretreatment MPNST to benign PN patients, we generated a receiver operating characteristic (ROC) curve of plasma tumor fraction. Tumor fraction values derived from ctDNA-enriched 90 to 150 bp fragments were compared to tumor fractions derived from all cfDNA fragment lengths. For ctDNA-enriched tumor fraction, an optimized cutpoint was determined by Youden's index (the point on the ROC curve that maximizes sensitivity+specificity−1), and high and low plasma tumor fraction groups by cutpoint were compared to clinical status by Fisher exact test. A logistic regression was also performed for the MPNST versus PN groups using the glm function in R, evaluating the effects of age, sex, and institution in addition to pretreatment plasma tumor fraction. Leave-one-out cross-validation was performed in R using the caret package. The reverse Kaplan-Meier method was used to estimate follow-up times. Statistical analyses were performed using R v.3.6.1 or Prism 9 (GraphPad Software).

Results

Genome-Wide CNAs from Tumor Detected in Plasma

Approximately 86% of the MPNST and PN patients met the NIH criteria for NF1 diagnosis. There was no difference in tumor fraction between the MPNST patients who met NIH criteria and those who did not (P=0.93 by Wilcoxon rank-sum test). Genomic copy number analysis of plasma cfDNA revealed that focal somatic CNAs that have previously been associated with PN tumor progression in NF1 patients were prominently observed in MPNST patients and were occasionally found in PN patients, but absent in healthy controls (FIGS. 10, 11A, 11B, and 11C). For example, focal losses of CDKN2A/B, MTAP, SMARCA2, and SUZ12, alterations shown to be associated with malignant transformation of PN were observed in plasma from MPNST patients. CDKN2B and SUZ12 losses were also found in two PN patients, while SMARCA2 appeared to be copy number neutral in plasma across the full PN cohort. Loss of SUZ12 correlated with NF1 loss, consistent with both genes' location in the 17.q11.2 genomic locus. Additionally, we observed broader copy number gains in chromosome arms 1q, 7p, 8q, 9q, and 17q as well as broad losses in arms 6p and 9p only in MPNST patient plasma, again consistent with previous findings from NF1 MPNST tumors (FIG. 11A). Finally, while many types of NF1 gene activation can underlie the NF1 disease process, we observed evidence of one of these, NF1 copy number loss, only within MPNST and PN patients (FIGS. 11A and 11B), but not in healthy donor controls (FIG. 11C).

Given the observed copy number changes in patient plasma, we next compared genome-wide CNAs and associated tumor fractions across specimen types. For MPNST cases where tumor, leukocyte, and plasma were all available, the observed copy number aberrations were most prominent in the tumor samples, but also detected in plasma cfDNA prior to treatment, with a pattern reflective of the original tumor (FIG. 17). The magnitude of these CNAs decreased in post-treatment cfDNA compared to pretreatment cfDNA, and germline samples harbored the least detectable CNAs. This trend also held for estimated tumor fractions, representing a sample's aggregate genome-wide copy number changes. As expected, there was no such increase in tumor fraction observed in PN lesions or in cfDNA derived from PN or healthy adults.

Plasma Tumor Fraction Distinguishes MPNST from Plexiform Neurofibroma

Figure 12A:
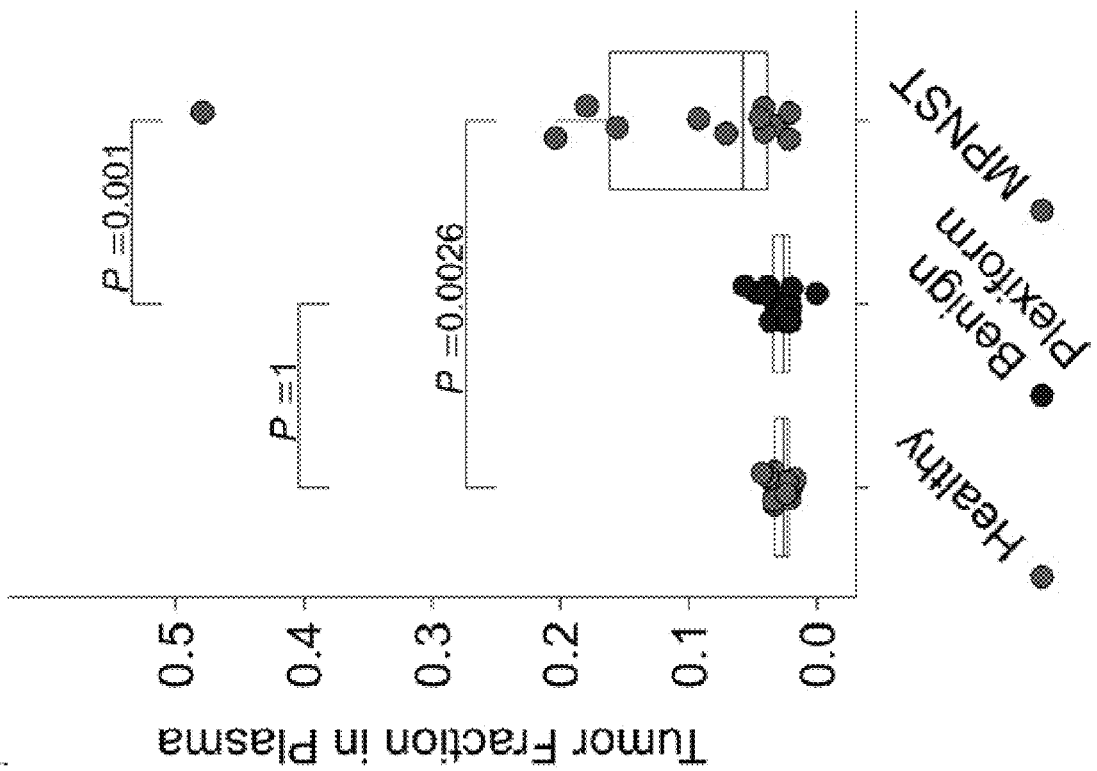
FIG. 12A is a graph comparing the tumor fractions estimated from copy number alterations detected from plasma samples using ULP-WGS for healthy control, PN, and MPNST subject groups.
Figure 20:
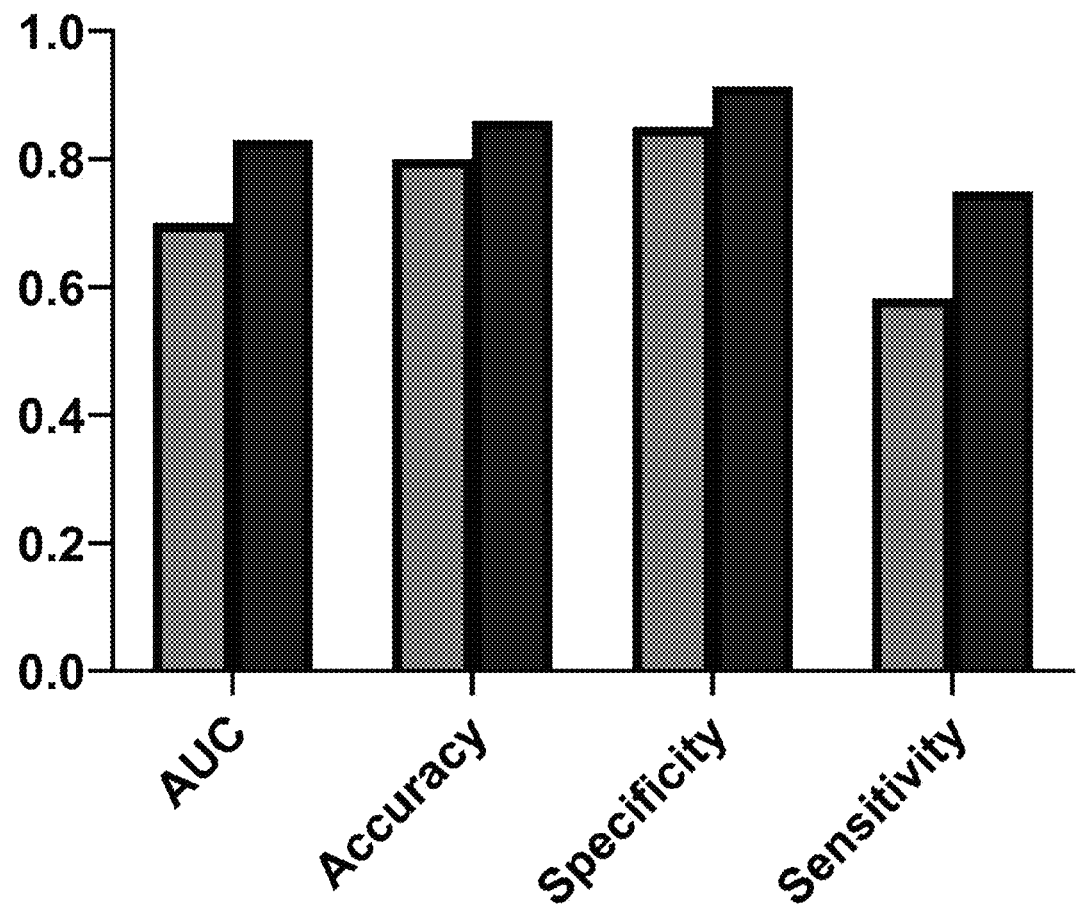
FIG. 20 is a bar graph comparing AUC, accuracy, specificity, and sensitivity of ROC summary statistics from 5 million paired reads (approximately 0.3× coverage) versus 10 million paired reads (approximately 0.6× coverage) followed by size selection of 90-150 bp cfDNA fragments.

Given that tumor-derived CNAs were detected in plasma cfDNA from MPNST patients, we next investigated the ability of plasma tumor fraction, inferred from the genome-wide copy number data following in silico size selection of 90 to 150 bp fragments, to noninvasively differentiate MPNST from PN. Plasma tumor fraction was compared between healthy controls, PN, and all pretreatment MPNST samples. Strikingly, baseline cfDNA tumor fraction differentiated MPNST from both healthy (P=0.0026) and PN (P=0.001) participants. PN and healthy donors did not differ in cfDNA tumor fraction (P=1) (FIG. 12A). Median tumor fraction levels in healthy (0.026) and PN (0.026) groups were lower than in MPNST (0.058). Comparing plasma tumor fractions between pretreatment MPNST patients and PN patients, ROC analysis further demonstrated an area under the curve (AUC) of 0.83 (FIG. 12B), which was higher with approximately 0.6×ULP-WGS than approximately 0.3× (FIG. 20). Notably, AUC decreased to 0.60 when considering all cfDNA fragment sizes, highlighting the importance of our in silico size selection step. This signified the ability to accurately discriminate between MPNST and PN using only plasma tumor fraction levels derived from ULP-WGS followed by in silico size selection.

Thus, utilizing a Youden's index-optimized cutpoint of 0.041, pretreatment plasma tumor fraction differentiated MPNST from PN with an area under the ROC curve of 0.83, and sensitivity of 75% and specificity of 91%, with 21 of 23 PN cases successfully classified based on pretreatment plasma tumor fraction alone (P=0.001), as summarized in Table 1 below. This result compared favorably to reports of other diagnostic modalities including MRI features and image-guided core-needle biopsy, as summarized in Table 2 below. Model performance was retained in leave-one-out cross-validation using a penalized regression model where overall accuracy was 75% (95% CI 66% to 83%) and improved to 89% with AUC of 0.89, Youden's index-optimized sensitivity of 83%, and specificity of 91% when considering the highest plasma tumor fraction measured per participant on serial time point analysis (Table 3). In a multivariate binary logistic regression model including age, sex, and institution, baseline plasma tumor fraction remained significantly associated with clinical status (P=0.04), while the other covariates were not (Table 4).

TABLE 1

Confusion matrix comparing cfDNA assay performance to pre-treatment MPNST vs. PN diagnosis.

|  |  | Predicted | |
| --- | --- | --- | --- |
|  |  | MPNST | PN |
| Diagnosis | MPNST | TP = 9 | FN = 3 |
|  | PN | FP = 2 | TN = 21 |

FN, false negative;
FP, false positive;
MPNST, malignant peripheral nerve sheath tumor;
PN, plexiform neurofibroma,
TN, true negative;
TP, true positive.

TABLE 2

Comparison of diagnostic tests' ability to distinguish MPNST from PN.

| Diagnostic Modality | Sensitivity | Specificity |
| --- | --- | --- |
| Anatomic MRI[1] | 90% | 61% |
| Image-guided biopsy[2] | 73% | 100% |
| cfDNA ULP-WGS (current study), pre-treatment | 75% | 91% |
| cfDNA ULP-WGS (current study), serial analysis | 83% | 91% |

Comparison of assay performance in the current study to published sensitivity and specificity for standard-of-care MPNST diagnostic tests.
[1]Wasa et al., 2010,
[2]Graham et al., 2019

TABLE 3

Assay performance with alternative ROC cutpoints and timepoints.

| Condition | Cutpoint | AUC | Sensitivity | Specificity | Accuracy |
| --- | --- | --- | --- | --- | --- |
| Youden's Index, pre-treatment | 0.0413 | 0.83 | 75% | 91% | 86% |
| Youden's Index, serial analysis | 0.0413 | 0.89 | 83% | 91% | 89% |
| Specificity 100%, pre-treatment | 0.0709 | 0.83 | 50% | 100% | 83% |
| Specificity 100%, serial analysis | 0.0709 | 0.89 | 58% | 100% | 86% |
| Sensitivity 92%, pre-treatment | 0.0219 | 0.83 | 92% | 30% | 51% |
| Sensitivity 92%, serial analysis | 0.0311 | 0.89 | 92% | 70% | 77% |
| Sensitivity 100%, pre-treatment | 0.0214 | 0.83 | 100% | 22% | 49% |
| Sensitivity 100%, serial analysis | 0.0219 | 0.89 | 100% | 30% | 54% |

Comparison of different cutpoints and conditions for the receiver operating characteristic (ROC) curve predicting MPNST vs. plexiform neurofibroma clinical status. Pre-treatment represents the baseline cfDNA data, while serial analysis represents the highest plasma-derived tumor fraction detected on serial analysis.

TABLE 4

Multivariate logistic regression predicting MPNST vs. plexiform neurofibroma clinical status.

| Variable | Odds ratio | 95% CI | P-value |
| --- | --- | --- | --- |
| Plasma tumor fraction | 4.41E32 | [5.86xE9-1.20E72] | 0.0407 |
| Age | 0.985 | [0.895-1.07] | 0.724 |
| Sex | 1.10 | [0.136-9.01] | 0.924 |
| Institution | 0.960 | [0.0884-11.4] | 0.973 |

Multivariate logistic regression for predicting diagnosis with covariates being plasma tumor fraction, age, sex and institution.

Figure 12C:
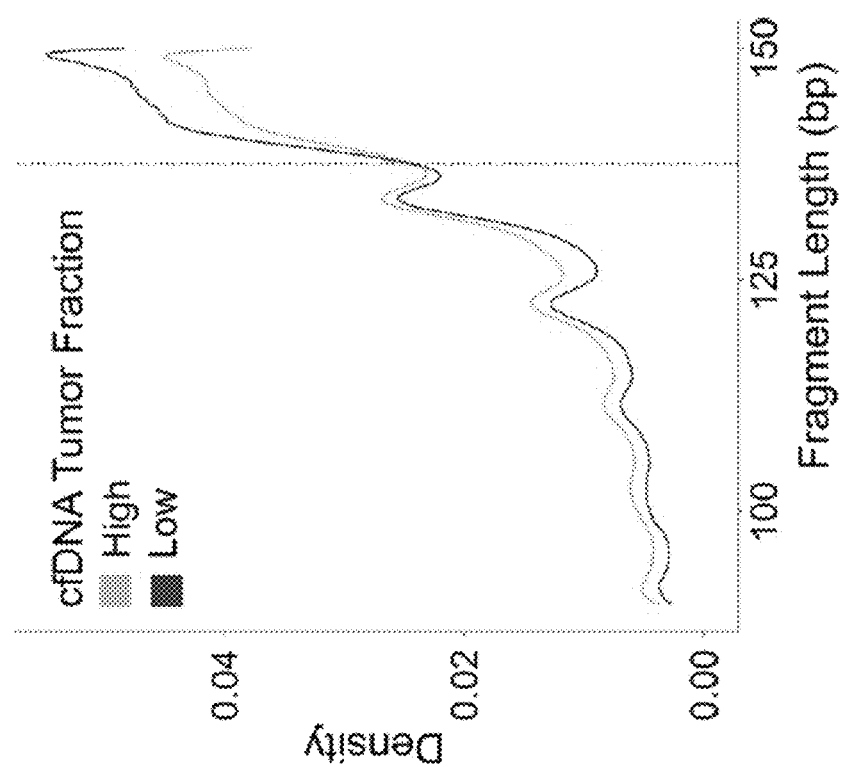
FIG. 12C is a graph comparing the Fragment length density for cfDNA in MPNST and PN patients (n=69 samples) with high (>0.0413) versus low (<0.0413) tumor fractions in plasma as determined by the Youden's index-optimized cutpoint from the ROC curve. The dashed line highlights an inflection in the curves with high tumor fraction samples enriched for shorter cfDNA fragment sizes (<138 bp) and low tumor fraction samples enriched for longer cfDNA fragment sizes (D=0.078, P<0.001 by two-sample Kolmogorov-Smirnov test). Data are shown for sequencing reads within the 90 to 150 bp in silico size-selection range.
Figures 18A, 18B:
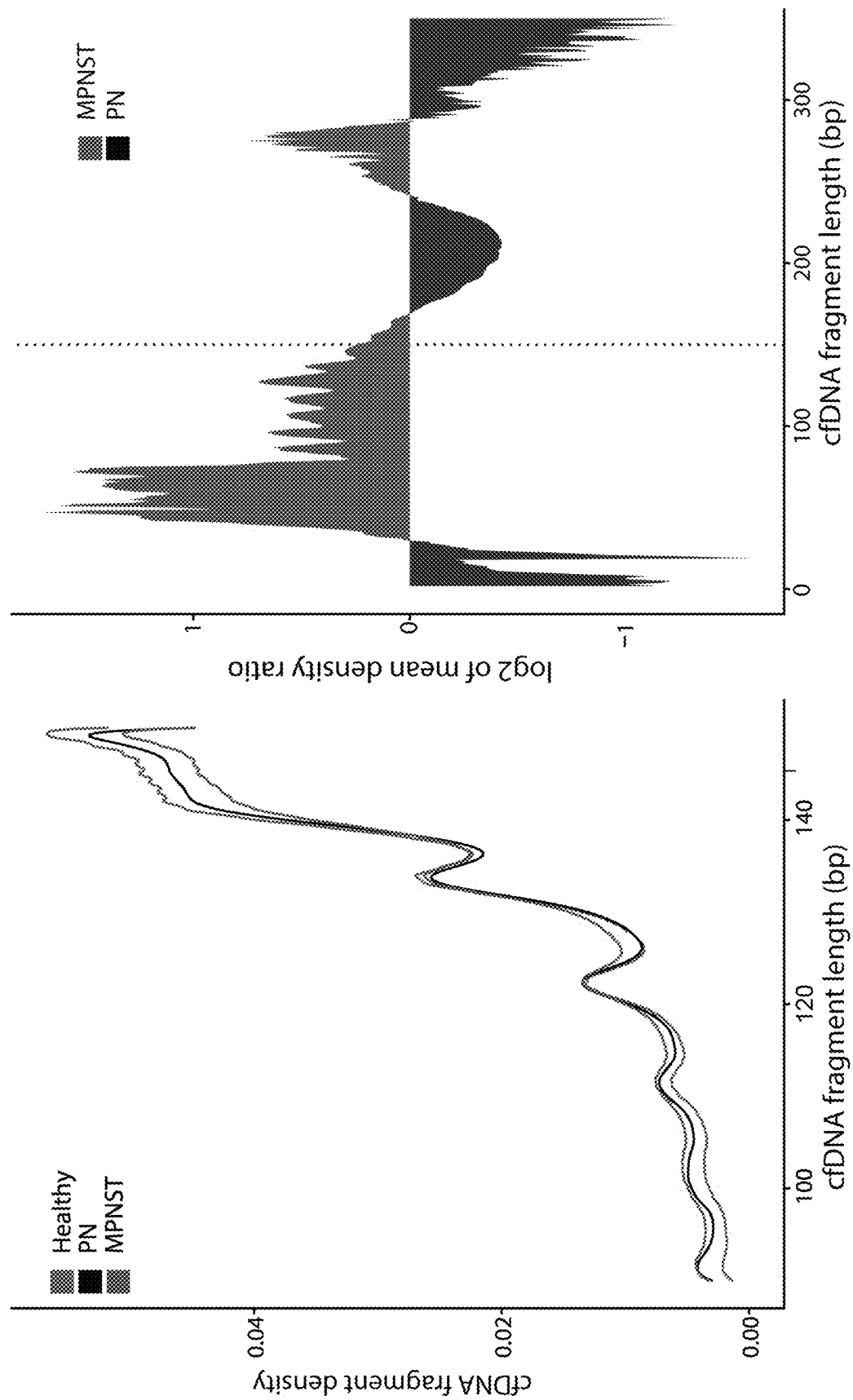
FIG. 18A is a graph comparing the plasma cfDNA fragment distributions of cfDNA from healthy donors, PN, and MPNST patients. cfDNA fragment sizes in MPNST patients were significantly shorter than from PN patients (D=0.032, P<0.001) or healthy donors (D=0.062, P<0.001), as determined by two-sample Kolmogorov-Smirnov testing.
FIG. 18B is a graph summarizing the Log 2 ratio of the differences in cfDNA fragment sizes from patients with MPNST versus PN with the dashed line indicating the upper boundary used for in silico size selection (150 bp).

Fragment size differences were observed between clinical states as defined by the tumor fraction ROC cutpoint. Using high-tumor fraction versus low-tumor fraction groups determined by the optimal cutpoint of 0.041, there was a significant difference in fragment length distributions (D=0.078, P<0.001 by two-sample Kolmogorov-Smirnov test) with high-plasma tumor fraction cases enriched for shorter cfDNA fragments and low-plasma tumor fraction cfDNA enriched for longer fragments (FIG. 12C). Similarly, clinically classified MPNST patients harbored significantly shorter cfDNA fragments compared to PN patients (D=0.032, P<0.001) and healthy donors (FIGS. 18A and 18B). Thus, fragmentation profiles appeared unique in patients with MPNST compared to those with benign PN.

Example 5

Correlation of MPNST Plasma Tumor Fraction with Radiologically-Derived Diseased Burden To assess whether the plasma tumor fraction obtained by ultra-low-pass whole genome sequencing (ULP-WGS) of a patient blood sample and subsequent analysis of copy number alterations (CNAs) as described in Example 4, the following experiments were conducted.

Having established plasma cfDNA fragment size and tumor fraction as a specific means to classify MPNST cases noninvasively in Example 4, we next investigated the relationship between plasma tumor fraction derived using our assay and radiologically measured tumor burden.

Patients with MPNST and PN were monitored by CT, MRI, and/or FDG-PET imaging at the treating institution at the managing clinicians' discretion. For patients with MPNST, radiographic tumor burden was quantified by sum of the longest tumor diameters (SLD) per RECIST 1.1 criteria. For comparison to serial time point cfDNA tumor fractions, each plasma sample was matched to the nearest SLD value at the primary institution within 30 days and without any interceding change of therapy. SLDs and plasma tumor fraction levels were then assessed using Pearson correlation coefficient. For comparisons of plasma tumor fraction to clinical status by RECIST, tumor fraction values were first normalized per patient to the lowest value detected on serial analysis, and then log 2 transformed to generate the final plotted values shown in FIG. 13B. Changes in clinical status were assessed and categorized as complete response, partial response, stable disease, or progressive disease per RECIST 1.1 criteria. RECIST 1.1 scoring was performed on serial imaging studies relative to a patient's baseline scan.

Figure 13A:
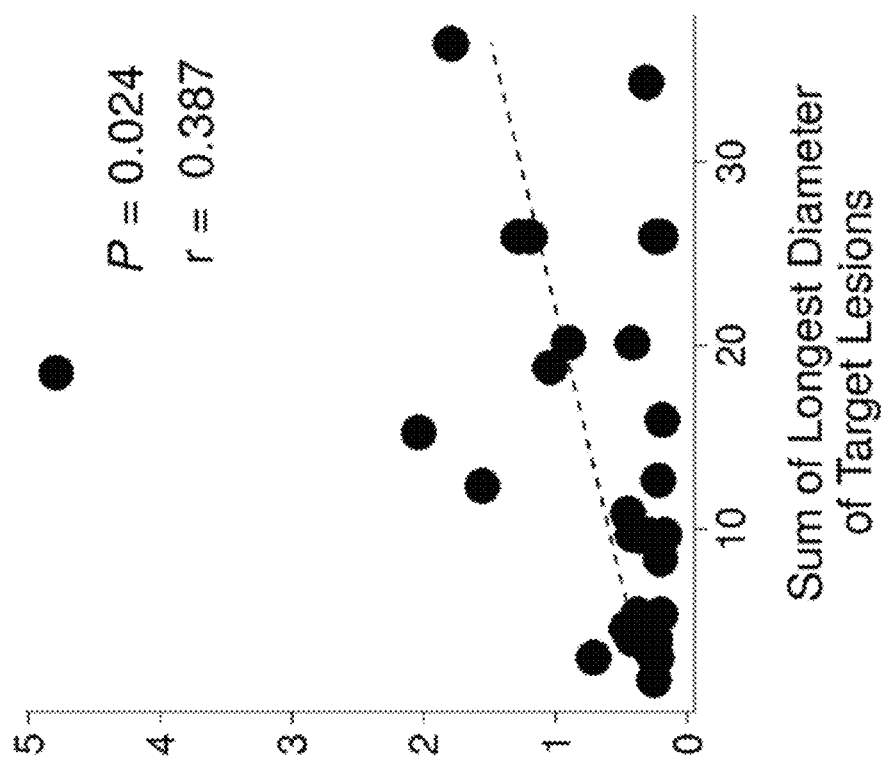
FIG. 13A is a graph summarizing the sum of longest tumor diameter (SLD) of target lesions for all MPNST patients plotted against each SLD's temporally closest plasma tumor fraction value; dashed line denotes a linear regression with a significant Pearson correlation coefficient (P=0.024).
Figure 13B:
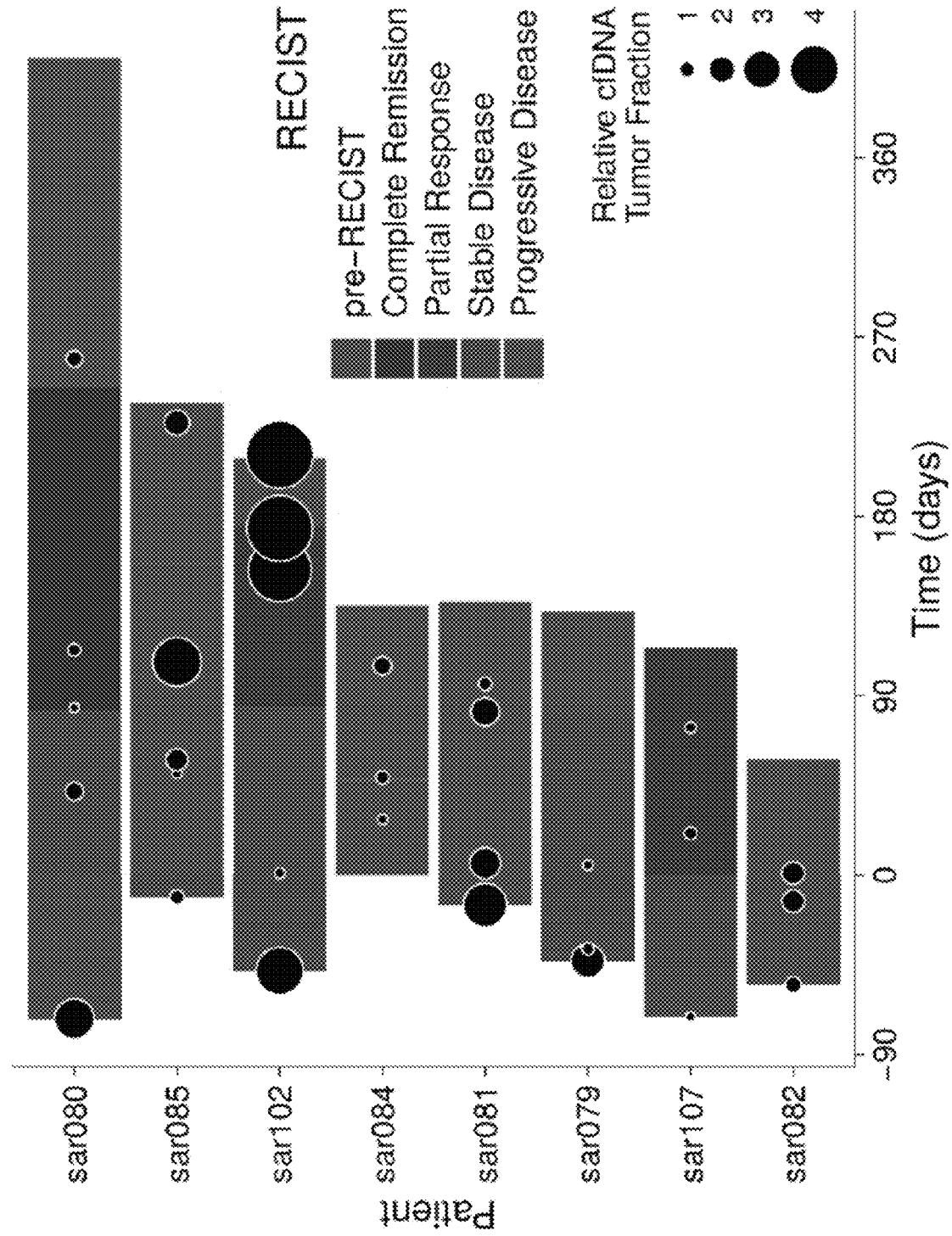
FIG. 13B is a graph comparing the timelines of RECIST classifications for MPNST patients that underwent serial monitoring (n=8) overlaid are cfDNA tumor fraction levels, normalized per patient to the lowest value detected on serial analysis, and then log 2 transformed.

A significantly positive correlation was observed between SLD and plasma tumor fraction (Pearson r=0.387, P=0.024) (FIG. 13A). Because RECIST SLD measurements were restricted to 5 total lesions, 2 lesions per organ and did not include bony disease, SLD may underestimate tumor burden in metastatic MPNST patients. Conversely, SLD may overestimate the size of malignant tissue in primary MPNST lesions, which often arise from within PN, with the relative contribution of PN versus MPNST tissue to the overall lesion size difficult to accurately assess radiographically. These challenges may limit the ability of SLD to accurately define MPNST disease burden and may explain why the correlation of SLD to tumor fraction was not stronger.

Figure 14:
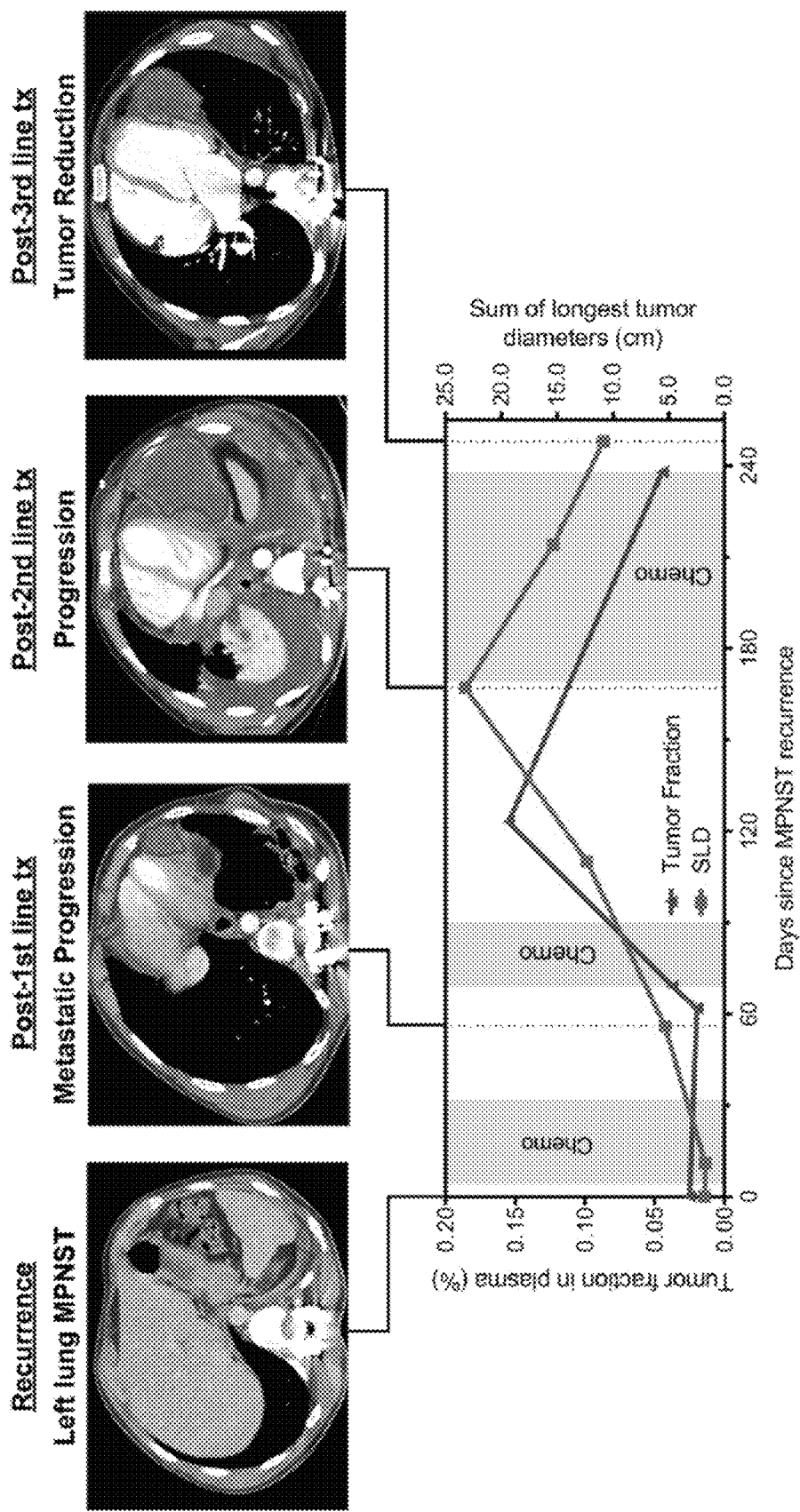
FIG. 14 is a graph summarizing the timelines of image-based SLDs and cfDNA tumor fraction levels for one MPNST patient diagnosed with a high-grade thoracic MPNST recurrence (t=0) that progressed rapidly through first- and second-line chemotherapy but responded to third-line chemotherapy. This figure further includes medical images obtained at t=0 and at three additional times over the course of treatment, as denoted by vertical dashed lines. Tumor fraction in plasma was initially undetectable, then rapidly increased during first- and second-line chemotherapy, followed by a rapid decrease during third-line chemotherapy. This dynamic tumor fraction in plasma correlated well with the SLD measured radiographically by RECIST 1.1 criteria.
Figure 19A:
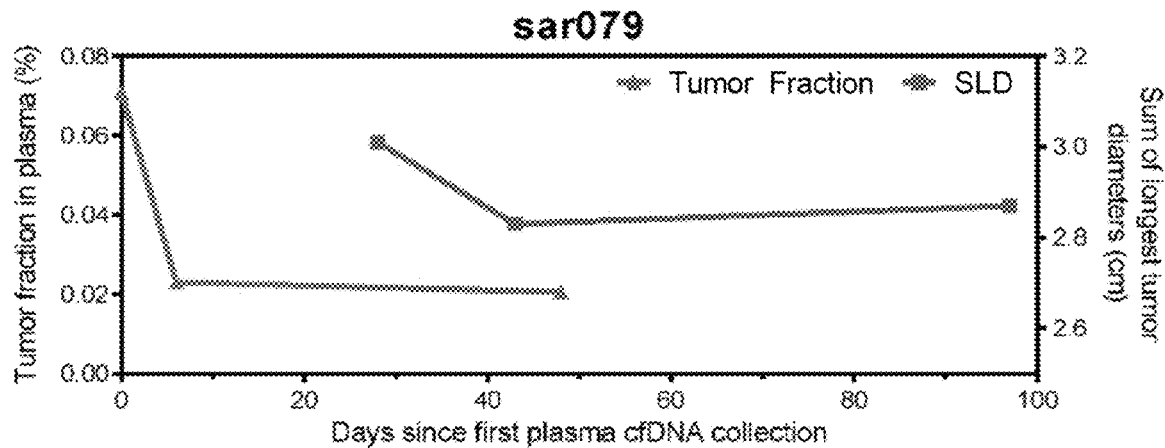
FIG. 19A is graph comparing the cfDNA tumor fraction (red) and SLD (blue) for a first MPNST patient tracked with serial plasma analysis.
Figure 19B:
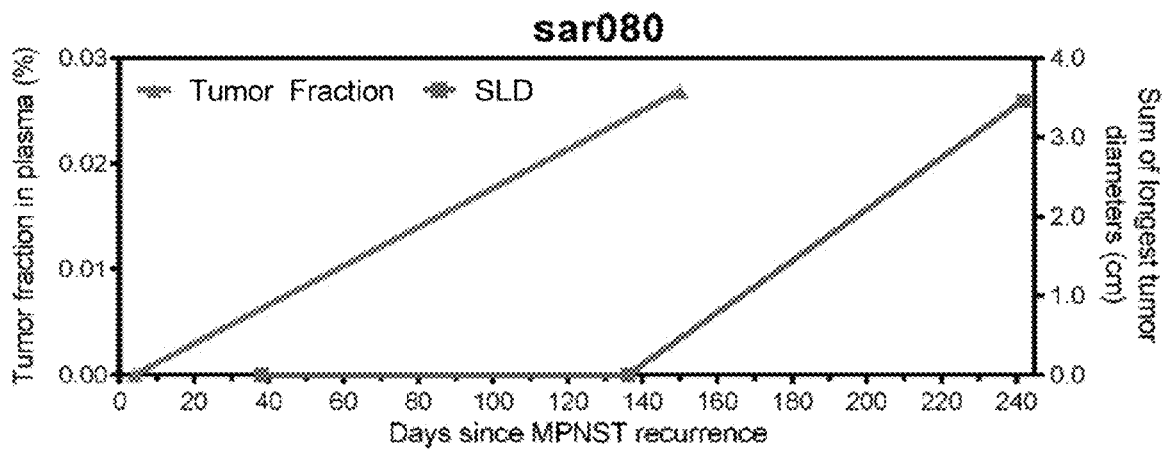
FIG. 19B is a graph comparing the cfDNA tumor fraction (red) and SLD (blue) for a second MPNST patient tracked with serial plasma analysis.
Figure 19C:
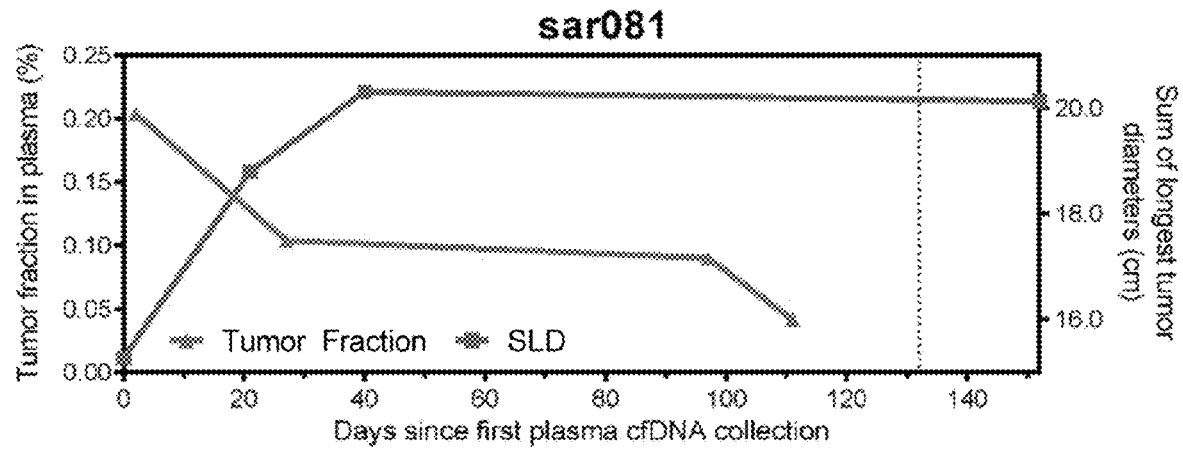
FIG. 19C is a graph comparing the cfDNA tumor fraction (red) and SLD (blue) for a third MPNST patient tracked with serial plasma analysis.
Figure 19D:
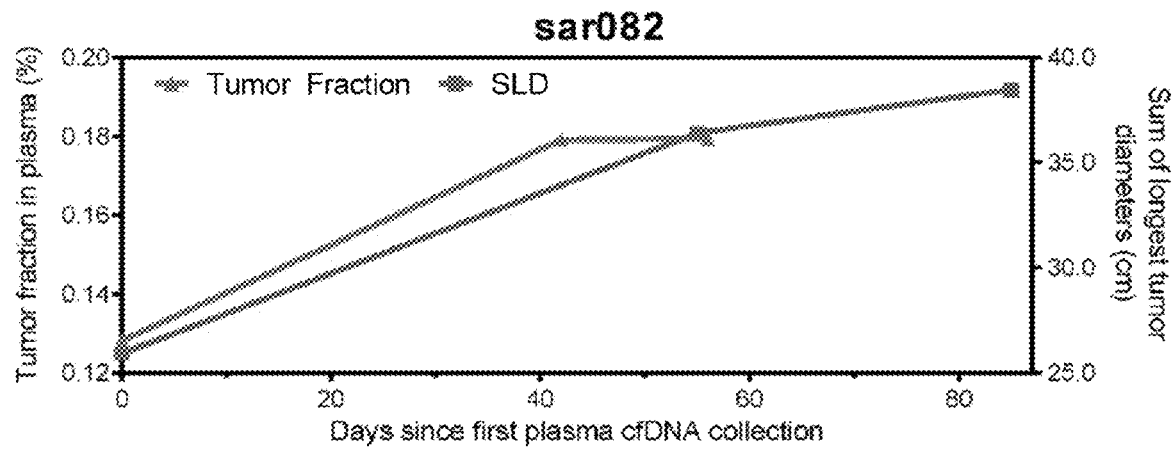
FIG. 19D is a graph comparing the cfDNA tumor fraction (red) and SLD (blue) for a fourth MPNST patient tracked with serial plasma analysis.
Figure 19E:
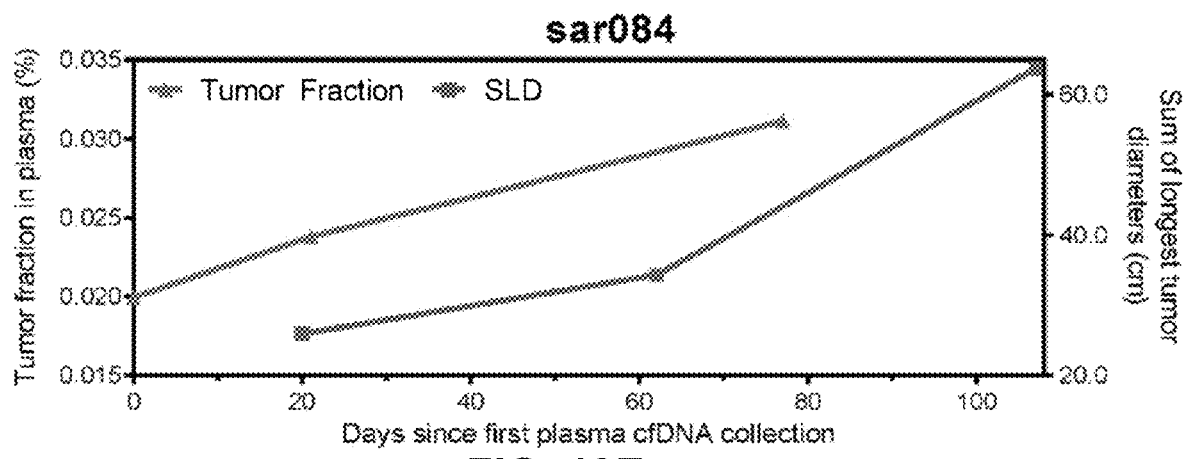
FIG. 19E is a graph comparing the cfDNA tumor fraction (red) and SLD (blue) for a fifth MPNST patient tracked with serial plasma analysis.
Figure 19F:
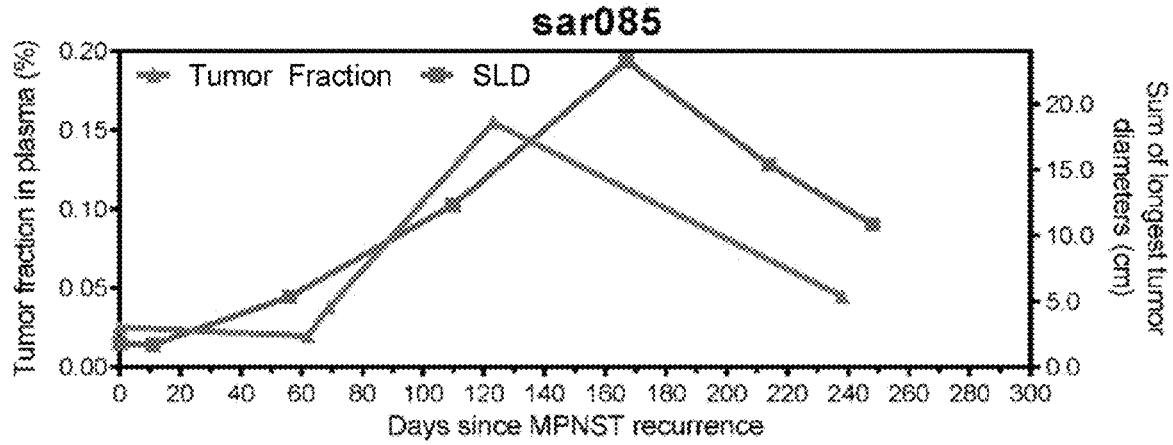
FIG. 19F is a graph comparing the cfDNA tumor fraction (red) and SLD (blue) for a sixth MPNST patient tracked with serial plasma analysis.
Figure 19G:
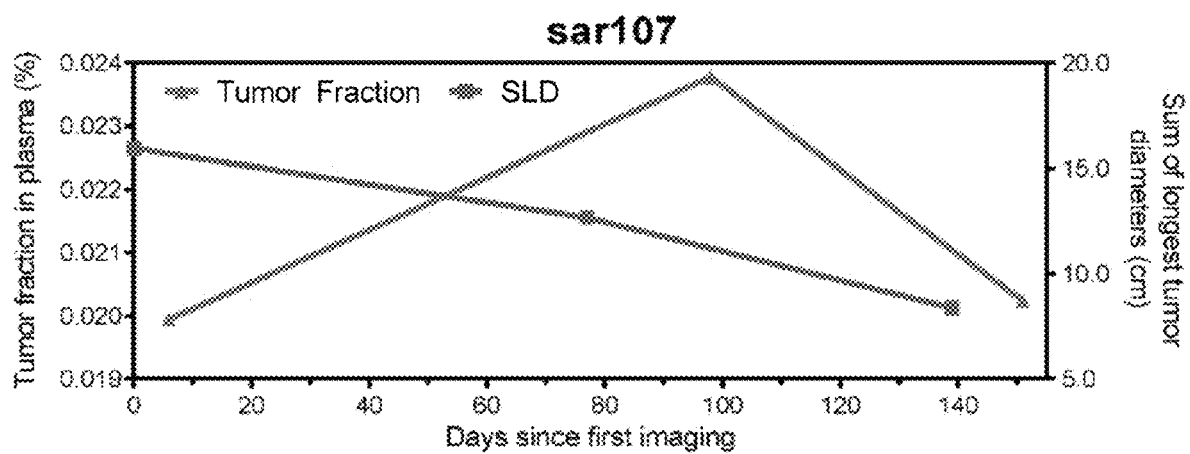
FIG. 19G is a graph comparing the cfDNA tumor fraction (red) and SLD (blue) for a seventh MPNST patient tracked with serial plasma analysis.
Figure 19H:
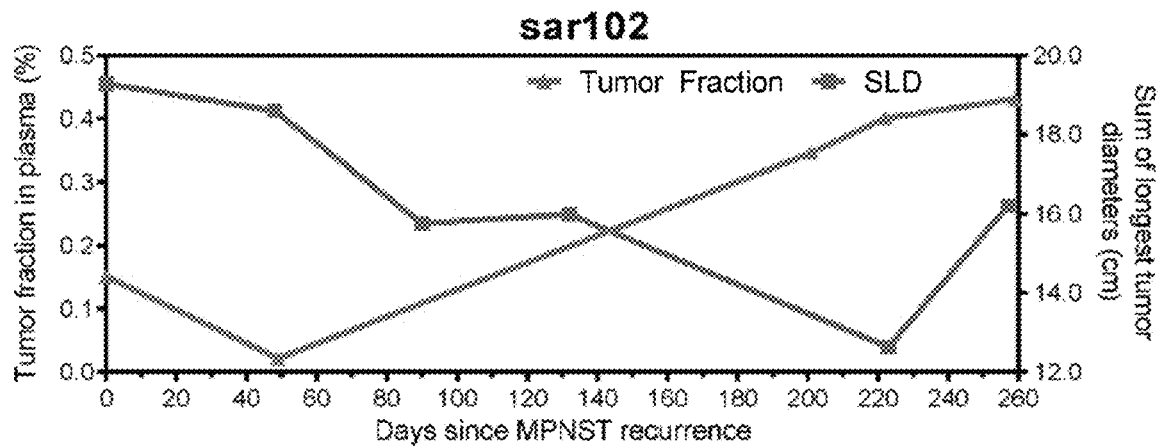
FIG. 19H is a graph comparing the cfDNA tumor fraction (red) and SLD (blue) for an eighth MPNST patient tracked with serial plasma analysis.

Both SLD and plasma tumor fractions were tracked over time in patients with serial time point data. RECIST 1.1 criteria were in these patients to classify radiographic response to therapy. Dynamic changes in plasma tumor fraction typically correlated with but preceded imaging changes (FIGS. 13B, 19A, 19B, 19C, 19D, 19E, 19F, 19G, and 19H). Timelines of disease progression versus response for MPNST patients were studied by comparing imaging SLD to plasma tumor fraction in the context of the specific treatments received (FIGS. 14, 15, 16, 19A, 19B, 19C, 19D, 19E, 19F, 19G, and 19H). For example, sar085 (FIG. 19F) presented with a small recurrent lung MPNST that rapidly progressed into multiple thoracic metastases despite 2 lines of cytotoxic chemotherapy, but then partially responded to third-line chemotherapy (FIG. 14). Interestingly, plasma tumor fraction levels closely tracked with SLD from CT imaging throughout this treatment course. These data suggest that plasma tumor fraction could thus be utilized to monitor treatment response.

Figure 15:
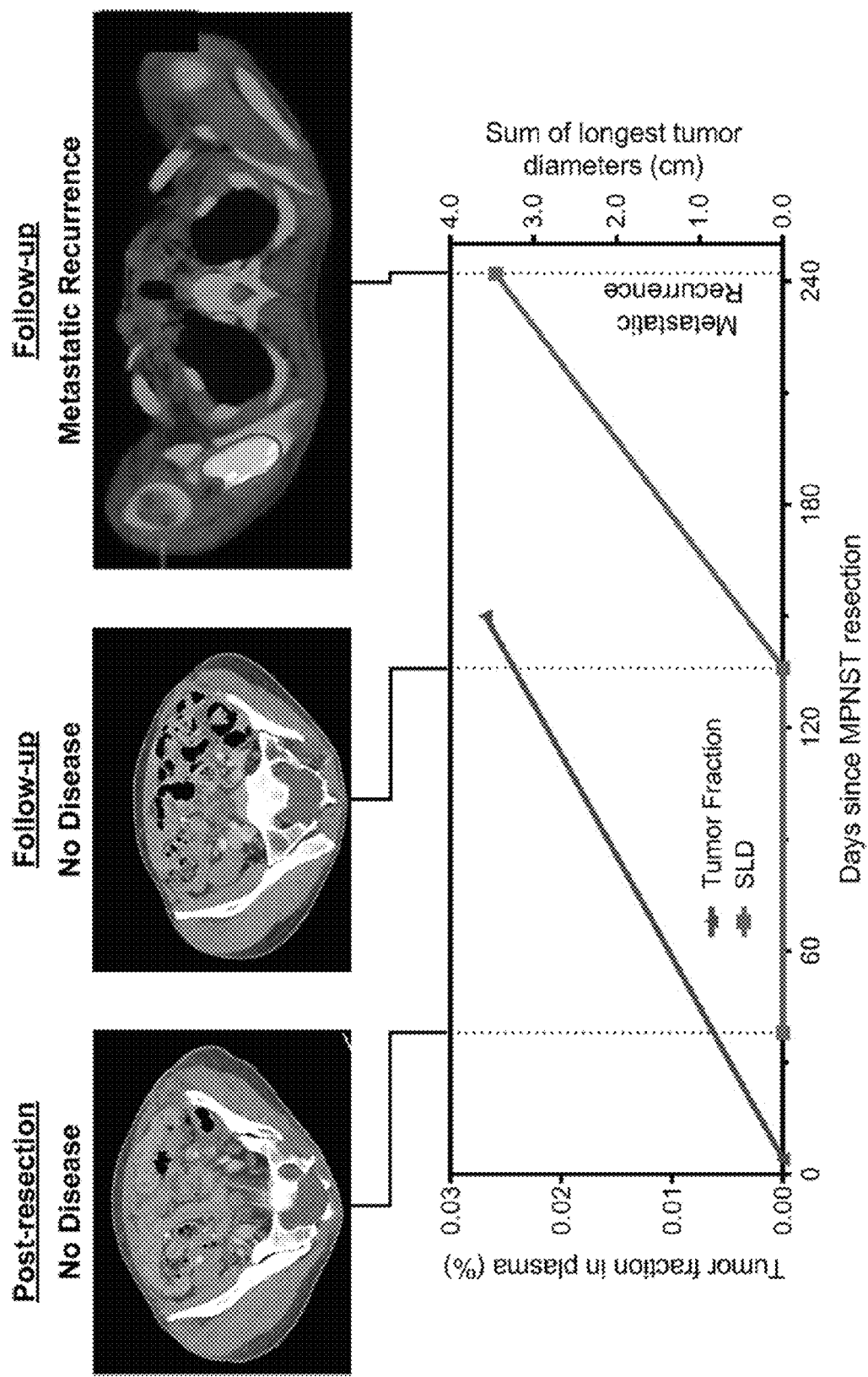
FIG. 15 is a graph summarizing the timelines of image-based SLDs and cfDNA tumor fraction levels for one MPNST patient a high-grade pelvic MPNST that was completely resected with no evidence of residual disease after surgery. Tumor fraction in plasma was undetectable following resection but was detected 150 days later (tumor fraction=0.021), 89 days prior to detecting the metastatic recurrence from surveillance imaging. This figure further includes medical images obtained at three additional times over the course of treatment, as denoted by vertical dashed lines.
Figure 16:
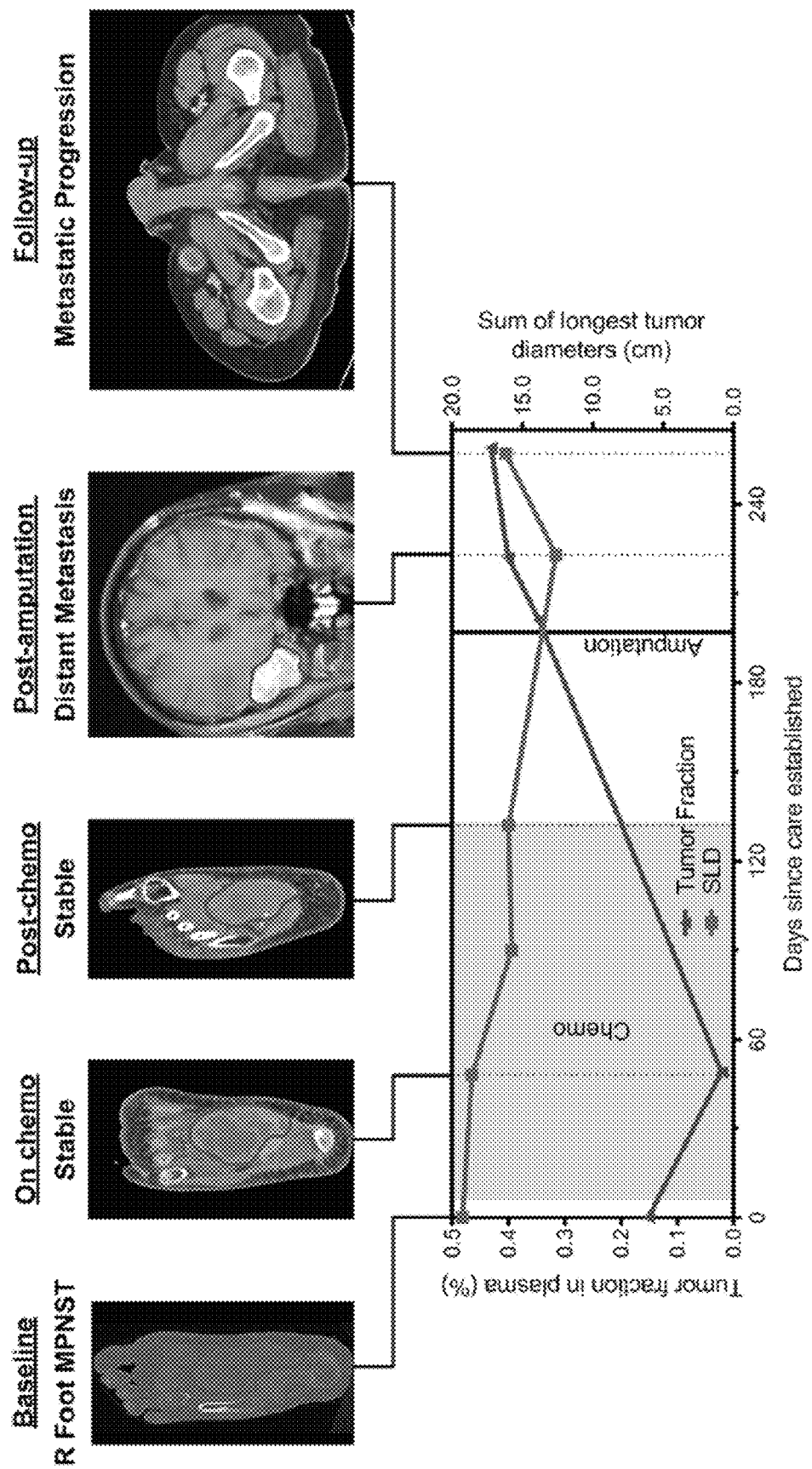
FIG. 16 is a graph summarizing the timelines of image-based SLDs and cfDNA tumor fraction levels for one MPNST patient diagnosed with a high-grade MPNST in the right foot that was deemed stable by imaging-based criteria and therefore had chemotherapeutic agents held in order to undergo an elective lower limb amputation for improved quality of life. Tumor fraction in plasma, however, increased during this presurgical time period, consistent with progressive metastatic disease, which became apparent on imaging shortly after surgery. The patient would not have had chemotherapy held to undergo lower limb amputation had there been earlier evidence of progressive metastatic disease. This figure further includes medical images obtained at t=0 and at four additional times over the course of treatment, as denoted by vertical dashed lines.

There were also several instances where cfDNA tumor fraction elevations anticipated and preceded corresponding SLD increases. sar080 (FIG. 19B) was an example in which the patient had complete resection of a right pelvic MPNST prior to plasma cfDNA analysis (FIG. 15). Initial plasma tumor fraction was not detected, which was consistent with a finding of no evidence of disease by imaging. Follow-up imaging again showed no evidence of disease 2.5 months later. Plasma tumor fraction rose, however, just 14 days later and preceded radiographic recurrence by 89 days, suggesting that the measurement of plasma tumor fraction could be utilized as a sensitive surveillance tool for minimal residual disease (MRD) detection following the completion of therapy.

sar102 (FIG. 19H) was another example where cfDNA tumor fraction elevation preceded radiographic progression. This patient had metastatic MPNST with a right foot primary tumor (FIG. 16). During and following over 4 months of cytotoxic chemotherapy, imaging showed a partial response with persistently decreasing SLD. Given radiographic evidence of disease control, the medical team then decided to hold cytotoxic chemotherapy for an elective lower limb amputation with the goal of improving quality of life (pain reduction and ability to use a prosthetic limb). In contrast to SLD, however, plasma tumor fraction increased 14-fold during this same interval. Following cessation of cytotoxic agents and amputation, the patient was found to have significant widespread tumor progression with the development of multiple distant metastases including brain metastases. Here, plasma tumor fraction was more consistent than serial imaging with this patient's ultimate clinical status and could have influenced the decision to hold chemotherapy in order to perform an elective, palliative amputation. This example illustrated the potential utility of plasma cfDNA tumor fraction analysis for dynamically monitoring disease, anticipating progression, and influencing clinical decision-making.

What is claimed is:

1. A method of selecting a treatment for a patient with Neurofibromatosis Type 1 (NF1) condition, the method comprising:
    a. providing a blood sample from the patient;
    b. isolating an amount of cell-free DNA (cfDNA) from the blood sample;
    c. performing ultra-low-pass whole genome sequencing (ULP-WGS) on the amount of cfDNA, wherein performing ULP-WGS comprises:
        i. fragmenting the amount of cfDNA to obtain a plurality of cfDNA fragments;
        ii. constructing a DNA library comprising the plurality of cfDNA fragments; and
        iii. sequencing the cfDNA fragments of the DNA library to obtain a plurality of reads, each read comprising a read sequence and a read fragment size corresponding to each cfDNA fragment;
    d. comparing a read fragment size distribution of the plurality of reads to a reference read fragment size distribution, the reference read fragment size distribution corresponding to a population of non-MPNST patients, wherein the read fragment size distribution and reference read fragment size distribution each comprise a distribution of fragment sizes ranging from about 90 bp to about 150 bp;
    e. predicting a transformation of the NF1 condition to a malignant peripheral nerve sheath tumor (MPNST) condition if the read fragment size distribution is enriched for shorter fragment sizes and depleted for longer fragment sizes; and, wherein the shorter fragment sizes comprise fragment sizes of less than about 138 bp and the larger fragment sizes comprise fragments of at least about 138 bp
    f. selecting a resection treatment for the patient if the transformation of the NF1 condition to the MPNST condition is predicted.

2. The method of claim 1, further comprising:
    a. aligning each read sequence of the plurality of reads to a reference human genome to obtain a plurality of aligned reads;
    b. estimating a plurality of local copy numbers based on the plurality of aligned reads;
    c. estimating a plurality of copy number alterations by comparing the plurality of local copy numbers to a plurality of reference copy numbers, wherein the reference copy numbers comprise local copy numbers obtained from a population of non-MPNST patients;
    d. estimating a tumor fraction of the patient based on the plurality of copy number alterations; and
    e. predicting the transformation of the NF1 condition to the MPNST condition if the tumor fraction is larger than a threshold value.

3. The method of claim 2, wherein the threshold value ranges from about 0.01 to about 0.05.

4. The method of claim 3, wherein the threshold value is about 0.041.

5. The method of claim 1, wherein the ULP-WGS is performed at a genomic coverage ranging from about 0.3× to about 0.6×.

6. The method of claim 4, further comprising estimating a disease burden of the patient based on predetermined correlation between the estimated tumor fraction and the disease burden.

7. A method of selecting a treatment for a patient with a Neurofibromatosis Type 1 (NF1) condition, the method comprising:

a. performing ultra-low-pass whole genome sequencing (ULP-WGS) on an amount of cfDNA isolated from a blood sample from the patient, wherein performing ULP-WGS comprises:
   i. fragmenting the amount of cfDNA to obtain a plurality of cfDNA fragments;
   ii. constructing a DNA library comprising the plurality of cfDNA fragments; and
   iii. sequencing the cfDNA fragments of the DNA library to obtain a plurality of reads, each read comprising a read sequence and a read fragment size corresponding to each cfDNA fragment;
b. aligning each read sequence of the plurality of reads to a reference human genome to obtain a plurality of aligned reads;
c. estimating a plurality of local copy numbers based on the plurality of aligned reads;
d. estimating a plurality of copy number alterations by comparing the plurality of local copy numbers to a plurality of reference copy numbers, wherein the reference copy numbers comprise local copy numbers obtained from a population of non-MPNST patients;
e. estimating a tumor fraction of the patient based on the plurality of copy number alterations; and
f. predicting a transformation of the NF1 condition to a malignant peripheral nerve sheath tumor (MPNST) condition if the tumor fraction is larger than a threshold value; and
g. selecting a resection treatment for the patient if the transformation of the NF1 condition to the MPNST condition is predicted.

8. The method of claim 7, wherein the read fragment size distribution and reference read fragment size distribution each comprise a distribution of fragment sizes ranging from about 90 bp to about 150 bp.

9. The method of claim 8, wherein the threshold value ranges from about 0.01 to about 0.05.

10. The method of claim 9, wherein the threshold value is about 0.041.

11. The method of claim 7, wherein the ULP-WGS is performed at a genomic coverage ranging from about 0.3× to about 0.6×.

* * * * *